(12) United States Patent
Trower et al.

(10) Patent No.: US 11,872,222 B2
(45) Date of Patent: Jan. 16, 2024

(54) USES

(71) Applicant: NeRRe Therapeutics Limited, Stevenage (GB)

(72) Inventors: Mike Trower, Stevenage (GB); Stephen Pawsey, Stevenage (GB); Mary Kerr, Stevenage (GB)

(73) Assignee: NeRRe Therapeutics Limited, Stevenage (GB)

( * ) Notice: Subject to any disclaimer, the term of this patent is extended or adjusted under 35 U.S.C. 154(b) by 267 days.

(21) Appl. No.: 17/333,415

(22) Filed: May 28, 2021

(65) Prior Publication Data

US 2021/0369707 A1 Dec. 2, 2021

Related U.S. Application Data

(60) Provisional application No. 63/033,279, filed on Jun. 2, 2020.

(51) Int. Cl.
*A61K 31/4985* (2006.01)
*A61K 9/00* (2006.01)
*A61K 9/20* (2006.01)

(52) U.S. Cl.
CPC ........ *A61K 31/4985* (2013.01); *A61K 9/0053* (2013.01); *A61K 9/2054* (2013.01)

(58) Field of Classification Search
None
See application file for complete search history.

(56) References Cited

U.S. PATENT DOCUMENTS

| | | | |
|---|---|---|---|
| 7,189,713 | B2 | 3/2007 | Alvaro et al. |
| 8,309,553 | B2 | 11/2012 | Beato et al. |
| 9,750,739 | B2 | 9/2017 | Trower |
| 2017/0326141 | A1 | 11/2017 | Trower |

FOREIGN PATENT DOCUMENTS

| | | | | |
|---|---|---|---|---|
| WO | 2004071429 | A2 | 8/2004 | |
| WO | WO-2017118584 | A1 * | 7/2017 | ........... A61K 31/194 |
| WO | WO-2018136554 | A1 * | 7/2018 | ........... A61K 31/403 |

OTHER PUBLICATIONS

Wu et al., Toxicology, vol. 236, pp. 1-6 (Year: 2007).*
Brégeon F. et al., "Substance P receptor blockade decreases stretch-induced lung cytokines and lung injury in rats," J. Physiol 588.8 (2010) pp. 1309-1319.
Chavolla-Calderón M et al., "Bone marrow transplantation reveals an essential synergy between neuronal and hemopoietic cell neurokinin production in pulmonary inflammation, " J. Clin. Invest. 111:973-980 (2003).
Fernandez I.E. et al., "The impact of TGF-beta on lung fibrosis from targeting to biomarkers, " Proc Am Thorac Soc vol. 9, Issue 3, pp. 111-116, Jul. 15, 2012.
Yonaga K et al., "Monocyte chemoattractant protein-1 in idiopathic pulmonary fibrosis and other interstitial lung diseases," Hum Pathol 25:455-463 (1994).
Kolahian S. et al., "Immune Mechanisms in Pulmonary Fibrosis," Am J Respir Cell Mol Biol vol. 55, Issue 3, pp. 309-322, Sep. 2016.
Obayashi Y et al., "The Role of Neutrophils in the Pathogenesis of Idiopathic Pulmonary Fibrosis" Chest, 1997; 112:1338-43.
Paine R. et al., "Cell Adhesion Molecules and Pulmonary Fibrosis," Am J Med. 1999; 268-279.
Zhang L et al., "Macrophages: friend or foe in idiopathic pulmonary fibrosis?", Respiratory Research (2018) 19:170.
Search Report and Written Opinion dated Aug. 31, 2021 in counterpart International Application PCT/IB2021/054686.
Wilson M.S. et al., "Pulmonary fibrosis: pathogenesis, etiology and regulation", Mucosal Immunology, vol. 2, No. 2, Mar. 1, 2009, pp. 103-121.

* cited by examiner

*Primary Examiner* — Zinna Northington Davis
(74) *Attorney, Agent, or Firm* — Silvia Salvadori, P.C.; Silvia Salvadori

(57) ABSTRACT

This invention relates to the new use of neurokinin-1 receptor antagonists as a treatment of pulmonary fibrosis conditions promoted by mechanical injury to the lungs. Specifically, when the mechanical injury to the lungs is induced by mechanical ventilation or by the act of coughing in a subset of patients with pulmonary fibrosis conditions who cough. The invention further relates to pharmaceutical compositions comprising neurokinin-1 receptor antagonist drugs and to combinations for such uses.

11 Claims, 3 Drawing Sheets

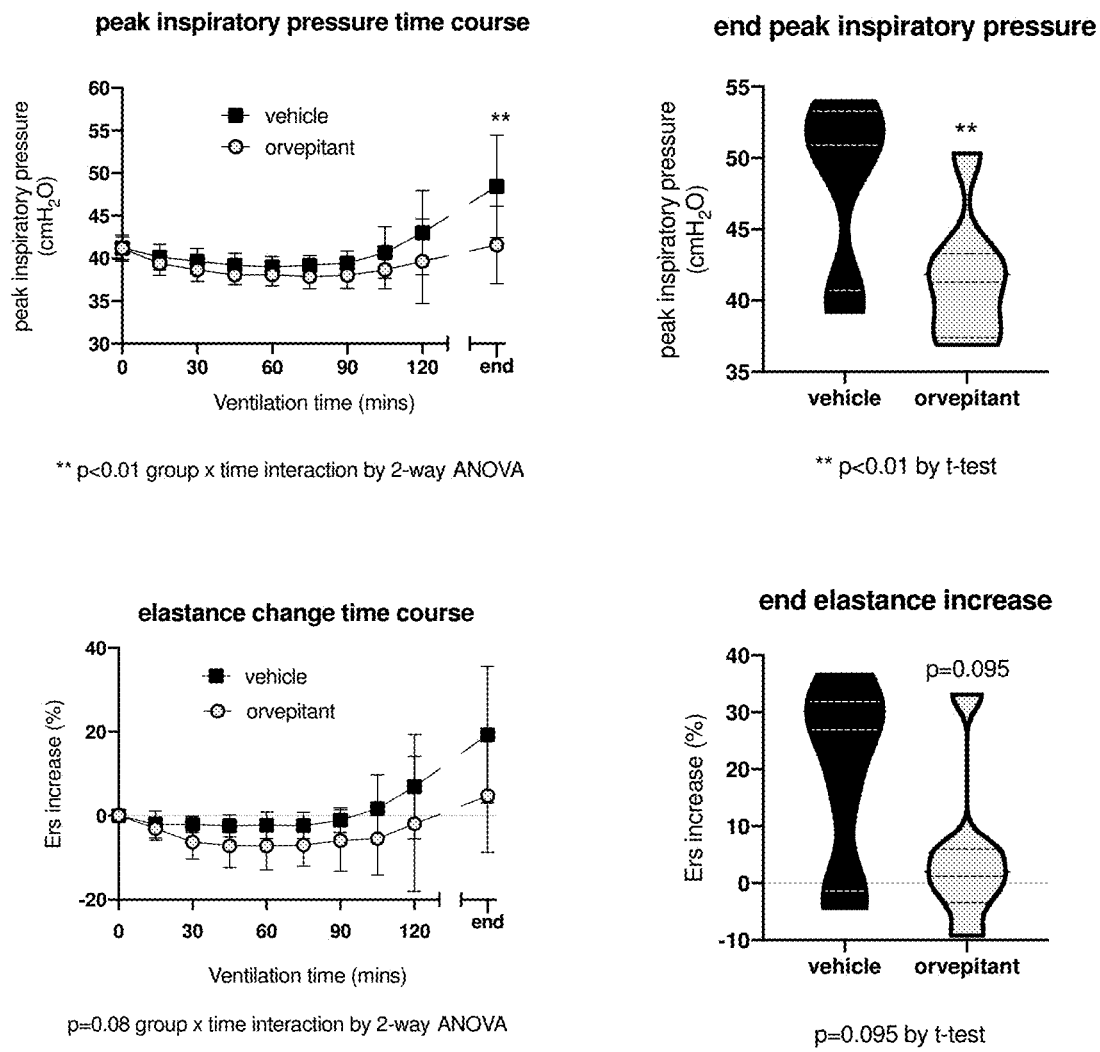
Figure 1. Physiological data of peak inspiratory pressure and elastance

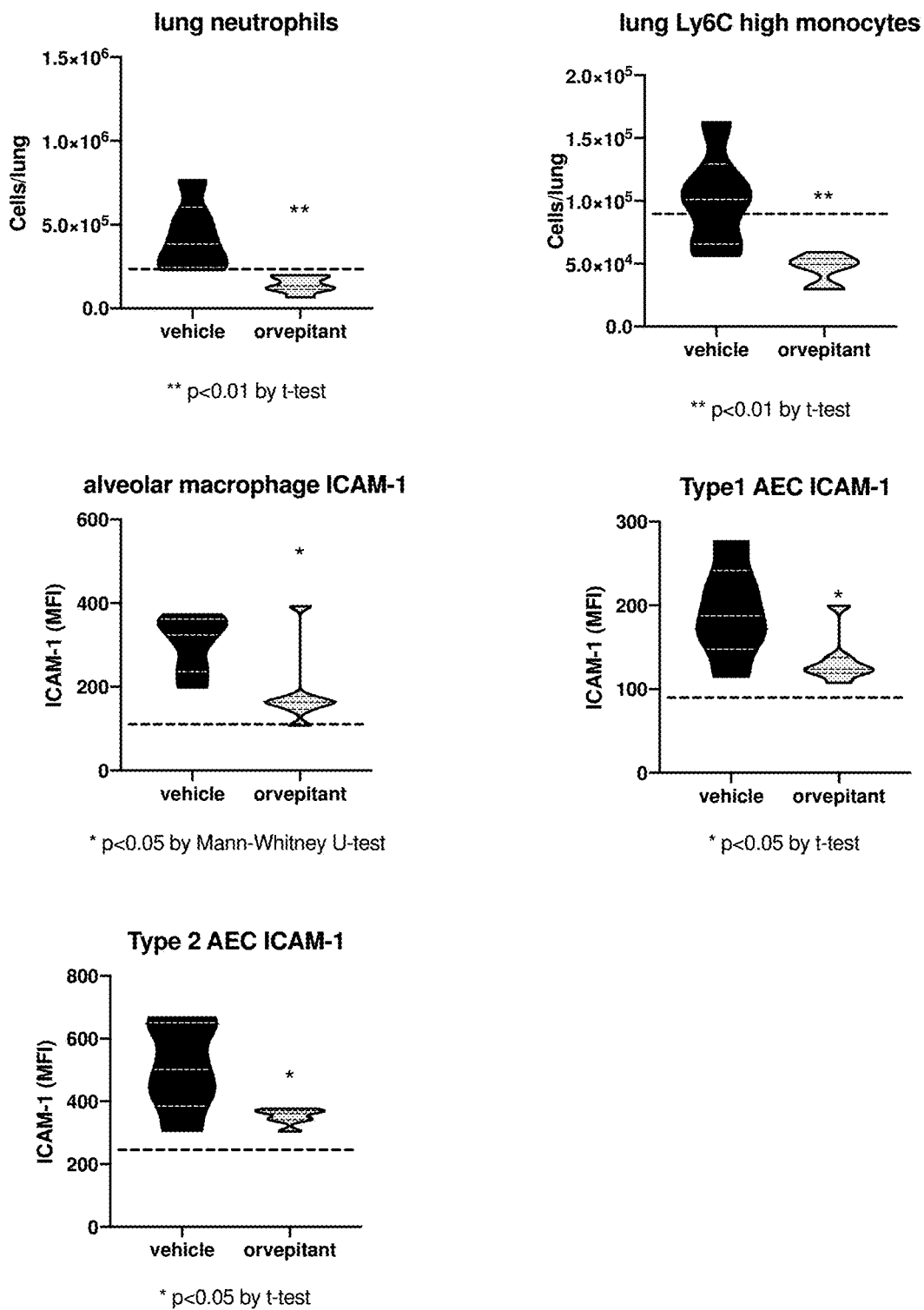
Figure 2. Flow cytometric analyses of lung white blood cells (WBCs) (neutrophils and Ly6C high inflammation monocytes [Ly6C$^{hi}$]) and surface expression of intercellular adhesion molecule-1 (ICAM-1) on aveolar macrophages, and Type 1 and 2 aveolar epithelial cells (AEC).

Figure 3. Bronchoalveolar lavage fluid (BAL) biomarkers. Assay of BAL total protein concentration, pro-inflammatory (monocyte chemoattractant protein-1 [MCP-1], interleukin-6 [IL-6]) and profibrotic transforming growth factor beta (TGF-$\beta$) mediators.
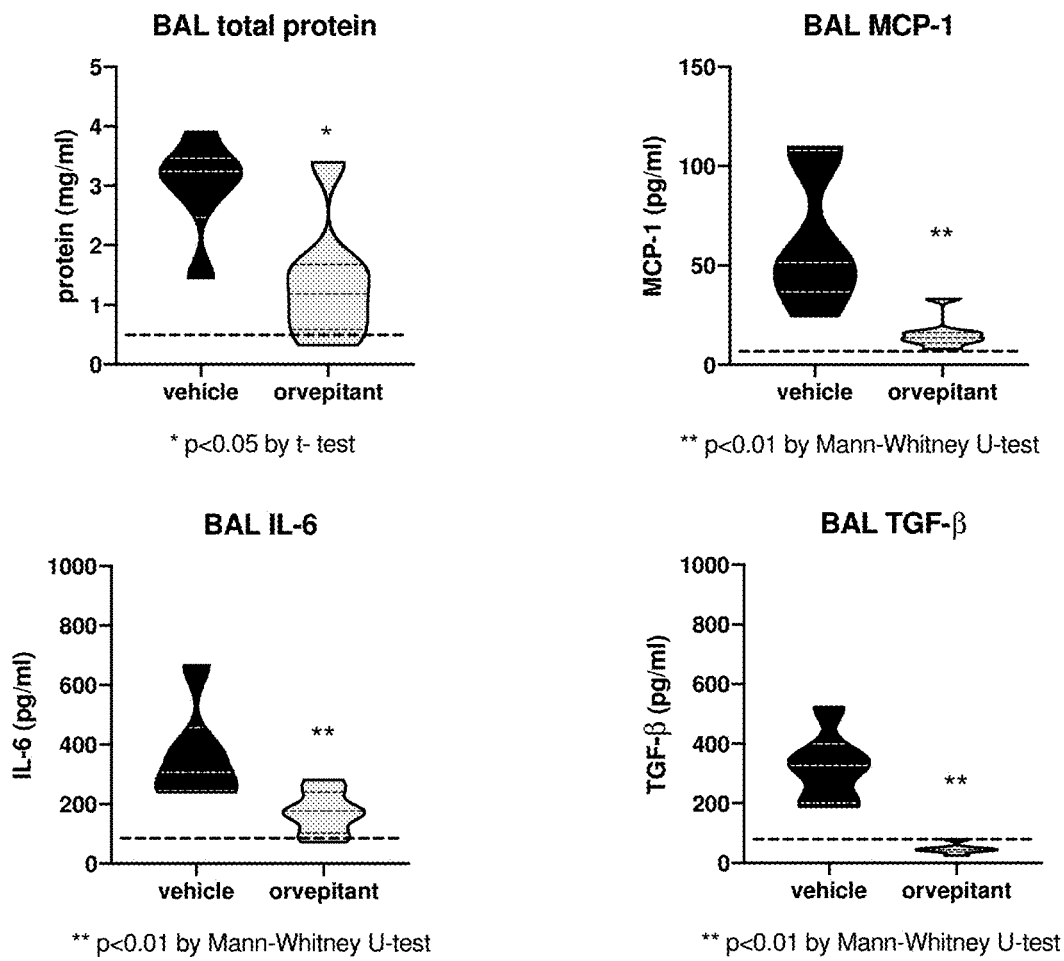

USES

This Non-Provisional Application claims priority to and the benefit of U.S. Provisional Application No. 63/033,279 filed on Jun. 2, 2020 the content of which is incorporated herein by reference in its entirety.

FIELD OF THE INVENTION

This invention relates to the new use of neurokinin-1 receptor antagonists as a treatment of pulmonary fibrosis conditions promoted by mechanical injury to the lungs. Specifically, when the mechanical injury to the lungs is induced by mechanical ventilation or by the act of coughing in a subset of patients with pulmonary fibrosis conditions who cough. The invention further relates to pharmaceutical compositions comprising neurokinin-1 receptor antagonist drugs and to combinations for such uses.

BACKGROUND OF THE INVENTION

The act of coughing induces much greater pressure changes than respiration alone and may therefore significantly amplify traction forces in the lung. The fibrotic lungs of patients with pulmonary fibrosis are three to five times stiffer compared with normal lungs and consequently have limited physical tolerance to expansion, and may therefore be particularly susceptible to mechanical injury from coughing. Coughing in patients with pulmonary fibrosis conditions could cause pressure injury (barotrauma), lung overdistension (volutrauma), shear stress on epithelial cells in the alveoli and/or small airways (atelectrauma) as well as additional lung and extra-pulmonary organ injury caused by the pro-injurious inflammatory response to the mechanical lung injury (biotrauma). Lung injury due to treatment with mechanical ventilation, may also cause barotrauma, volutrauma, atelectrauma with the resulting biotrauma leading to ventilator-induced lung injury (VILI).

Pulmonary fibrosis conditions that may be promoted by mechanical injury to the lungs are serious illnesses that often become progressively worse, may require lung transplantation and are very often fatal. There are no available therapies to address the contribution of mechanical injury to the lungs to the development and progression of these debilitating conditions associated with such substantial levels of morbidity and mortality.

Therefore, it is an object of the invention to provide compositions and methods of use thereof for treating the pathophysiological processes associated with the onset and progression of pulmonary fibrosis conditions promoted by mechanical injury to the lungs in a subject.

SUMMARY OF THE INVENTION

The solution provided by the present invention is the use of neurokinin (NK)-1 receptor antagonists as a treatment of pulmonary fibrosis conditions promoted by mechanical injury to the lungs.

Particularly, it has been found that NK-1 receptor antagonists could be effective anti-fibrotic treatments in the subset of patients with pulmonary fibrosis conditions who cough.

It has also been found that NK-1 receptor antagonists could be effective treatments for mechanical ventilator induced pulmonary fibrosis conditions.

Thus, in one aspect, this invention provides a method of treating pulmonary fibrosis conditions promoted by mechanical injury to the lungs in a patient in need of such treatment comprising administering to said patient a therapeutically effective amount of an NK-1 receptor antagonist.

In another aspect, the invention provides a method of treating pulmonary fibrosis conditions promoted by mechanical injury to the lungs in a patient in need of such treatment comprising administering to said patient a therapeutically effective amount of an NK-1 receptor antagonist and one or more pharmaceutically acceptable carriers or excipients.

In a further aspect, the invention provides a method of treating pulmonary fibrosis conditions promoted by mechanical injury to the lungs in a patient in need of such treatment comprising administering to said patient a therapeutically effective amount of an NK-1 receptor antagonist in combination with one or more therapeutic agents.

In one aspect, this invention provides a method of treating pulmonary fibrosis conditions in subjects in need thereof, wherein said subjects belong to a subset of patients with patients with pulmonary fibrosis conditions who cough, or patients with pulmonary fibrosis conditions who exacerbate their pulmonary fibrosis as a result of mechanical ventilation, or patients with acute respiratory failure that develop a pulmonary fibrosis condition as a result of mechanical ventilation; and wherein the method comprises administering to said patients a therapeutically effective amount of an NK-1 receptor antagonist.

In another aspect, this invention provides a method of treating pulmonary fibrosis conditions in subjects in need thereof, wherein said subjects belong to a subset of patients with pulmonary fibrosis conditions who cough, or patients with pulmonary fibrosis conditions who exacerbate their pulmonary fibrosis as a result of mechanical ventilation, or patients with acute respiratory failure who develop a pulmonary fibrosis condition as a result of mechanical ventilation, and wherein the method comprises administering to said patient a therapeutically effective amount of an NK-1 receptor antagonist and one or more pharmaceutically acceptable carriers or excipients.

In a further aspect, this invention provides a method for amelioration of symptoms associated with the release of proinflammatory and profibrotic mediators following mechanical injury to the lungs of patients with pulmonary fibrosis conditions who cough or as a result of mechanical ventilation in patients with either pulmonary fibrosis conditions or acute respiratory failure.

According to another aspect, there is provided a method of reducing the release of such proinflammatory and profibrotic mediators following mechanical injury to the lungs of patients with pulmonary fibrosis conditions who cough or as a result of mechanical ventilation in patients with either pulmonary fibrosis conditions or acute respiratory failure, comprising the step of administering to a subject in need thereof a therapeutically effective amount of an NK-1 receptor antagonist, or a pharmaceutically acceptable salt or a derivative thereof.

BRIEF DESCRIPTION OF THE DRAWINGS

FIG. 1 shows physiological data of peak inspiratory pressure and elastance.

FIG. 2 shows flow cytometric analyses of lung neutrophils, white blood cells (WBCs) and lung Ly6C high inflammation [Ly6C$^{hi}$] monocytes and surface expression of intercellular adhesion molecule-1 (ICAM-1) on both aveolar macrophages, and Type 1 and 2 aveolar epithelial cells (AEC).

FIG. 3. shows bronchoalveolar lavage fluid (BAL) biomarkers. Assay of BAL total protein concentration, proinflammatory (monocyte chemoattractant protein-1 [MCP-1], interleukin-6 [IL-6]) and profibrotic transforming growth factor beta (TGF-β) mediators.

Data in the FIGS. 1-3 are shown as mean±standard deviation for time course data or violin plots (with lines indicating median and upper/lower quartiles) for end-point analyses. Dotted lines on graphs represent mean/median data as appropriate from vehicle-treated, low tidal volume ventilated animals for comparison.

DETAILED DESCRIPTION OF THE INVENTION

While various embodiments of the present disclosure are described herein, it will be obvious to those skilled in the art that such embodiments are provided by way of example only. Numerous modifications and changes to and variations and substitutions of the embodiments described herein will be apparent to those skilled in the art without departing from the disclosure. It is understood that various alternatives to the embodiments described herein may be employed in practicing the disclosure. It is also understood that every embodiment of the disclosure may optionally be combined with any one or more of the other embodiments described herein which are consistent with that embodiment.

It is further understood that, in general, where an embodiment in the description or the claims is referred to as comprising one or more features, the disclosure also encompasses embodiments that consist of, or consist essentially of, such feature(s).

It is further understood that the present disclosure encompasses analogs, derivatives, prodrugs, metabolites, salts, solvates, hydrates, clathrates and polymorphs of all of the compounds/substances disclosed herein, as appropriate. The specific recitation of "analogs", "derivatives", "prodrugs", "metabolites", "salts", "solvates", "hydrates", or "polymorphs" with respect to a compound/substance or a group of compounds/substances in certain instances of the disclosure shall not be interpreted as an intended omission of any of these forms in other instances of the disclosure where the compound/substance or the group of compounds/substances is mentioned without recitation of any of these forms.

All patent literature and all non-patent literature cited herein are incorporated herein by reference in their entirety to the same extent as if each patent literature or non-patent literature were and individually indicated to be incorporated herein by reference in its entirety.

Definitions

Unless defined otherwise or indicated otherwise by their use herein, all technical and scientific terms used herein have the same meaning as commonly understood by one of ordinary skill in the art to which this application belongs.

All numbers expressing quantities, percentages or proportions, and other numerical values used in the specification and claims, are to be understood as being modified in all instances by the term "about."

It should be understood that the terms "a" and "an" as used herein refer to "one or more" of the enumerated components. It will be clear to one of ordinary skill in the art that the use of the singular includes the plural unless stated otherwise.

As used herein, the terms "treatment," "treating," and the like, refer to obtaining a desired pharmacologic, physiologic, dermatologic or cosmetic effect. The effect may be prophylactic in terms of completely or partially preventing a condition or disease or disorder or adverse symptom thereof; and/or may be therapeutic in terms of a partial or complete halt to the progression of a condition or disease or disorder and/or adverse symptom or effect attributable to the condition or disease or disorder; and/or may be therapeutic in terms of a partial or complete cure for a condition or disease or disorder and/or adverse symptom or effect attributable to the condition or disease or disorder. It will be appreciated that the effect attributable to the condition or disease or disorder includes the longer-term sequelae of the disorder and/or adverse symptom or effect attributable to the condition or disease or disorder. Reference to "treatment" of a medical condition includes preventing (precluding), reducing the risk of developing, delaying the onset of, and slowing the progression of, the condition or one or more symptoms or complications associated with the condition.

The terms "treatment," "treating," and the like also mean prolonging survival as compared to expected survival if not receiving treatment, improving quality of life, and reducing health care costs and utilisation.

"Treatment," thus, for example, covers any treatment of a condition or disease in a mammal, particularly in a human, and includes: (a) preventing the condition or disease, disorder or symptom thereof from occurring in a subject which may be predisposed to the condition or disease or disorder but has not yet been diagnosed as having it; (b) inhibiting the condition or disease, disorder or symptom thereof, such as, arresting its development; and (c) slowing the condition or disease, disorder or symptom thereof, such as, slowing its progression; and (d) relieving, alleviating or ameliorating the condition or disease or disorder or symptom thereof, such as, for example, causing regression of the condition or disease or disorder or symptom thereof.

As used herein, the term "effective amount" means that amount of a drug or pharmaceutical agent that will elicit the biological or medical response of a tissue, system, animal or human that is being sought, for instance, by a researcher, clinician or veterinarian.

The term "antitussive" means to prevent or relieve a cough.

The term "the subset of patients who cough" refers to those patients who have a burden of cough greater than a healthy individual.

The term "NK-1 receptor" refers to a member of the G protein-coupled superfamily of receptors called tachykinin receptors. The tachykinins, also called neurokinins, are a family of peptide neurotransmitters that mediate the release of intracellular calcium by binding to a group of transmembrane receptors called neurokinin (NK) receptors. Mammalian tachykinin receptors consist of three types: Neurokinin-1 (NK-1), Neurokinin-2 (NK-2), and Neurokinin-3 (NK-3) receptors. Substance P (SP) is the cognate agonist ligand of the NK-1 receptor, which is also known as the SP receptor, though other tachykinins can bind the NK-1 receptor with lower affinity. Antagonists of the NK-1 receptor, are thus of use in the treatment of conditions mediated by tachykinins, in particular SP.

The term "pharmaceutically acceptable" refers to those compounds (or salts, prodrugs, tautomers, zwitterionic forms, etc.) which are suitable for use in contact with the tissues of patients without excessive toxicity, irritation, allergic response, immunogenicity, are commensurate with a reasonable benefit/risk ratio, and are effective for their intended use.

As used herein, "pharmaceutically acceptable excipient" or "pharmaceutically acceptable carrier" mean a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound according to the invention when administered to a patient and interactions which would result in pharmaceutical compositions that are not pharmaceutically acceptable are avoided. In addition, each excipient must of course be pharmaceutically acceptable e.g. of sufficiently high purity.

The term "therapeutically effective amount" refers to an amount of a substance that, when administered to a subject, is sufficient to prevent reduce the risk of developing, delay the onset of, or slow the progression of the medical condition being treated, or to alleviate to some extent one or more symptoms or complications of that condition. The term "therapeutically effective amount" also refers to an amount of a substance that is sufficient to elicit the biological or medical response of a cell, tissue, organ, system, animal or human which is sought by a researcher, veterinarian, medical doctor or clinician.

The term "subject" refers to an animal, including a mammal, such as a primate (e.g., a human, a chimpanzee or a monkey), a rodent (e.g., a rat, a mouse, a guinea pig, a gerbil or a hamster), a lagomorph (e.g., a rabbit), a swine (e.g., a pig), an equine (e.g., a horse), a canine (e.g., a dog) or a feline (e.g., a cat).

The terms "subject" and "patient" are used interchangeably herein in reference, e.g., to a mammalian subject, such as a human subject.

The term relating to the lungs and pulmonary are intended to have the same meaning and are used interchangeably herein.

The term lungs include the pair of serous membranes that envelopes this organ called the pleura.

The term pleural means relating to the pleura and the two are intended to have the same meaning and are used interchangeably herein.

The term fibrotic means characterized by or affected with fibrosis and the two are intended to have the same meaning and are used interchangeably herein.

The terms pulmonary fibrosis, lung fibrosis, fibrotic lung disease, lung fibrotic disease, lung fibroproliferative disease, pulmonary fibroproliferative disease, fibroproliferative lung disease, fibroproliferative pulmonary disease, lung scarring and pulmonary scarring, are intended to have the same meaning and are used interchangeably herein.

The terms "mechanical injury" to the lungs, to lung tissues, to lung parenchyma, to lung interstitium, to lung cells, to pulmonary tissues, to pulmonary cells, to cells located in the lung, are intended to have the same meaning and are used interchangeably herein.

The term "mechanical injury to the lungs" includes mechanical injury to the lung pleura, to the airways and to the respiratory system.

The term "mechanical injury to the lungs" refers to damage to the lung caused by exceeding its physical tolerance, as a result of barotrauma (high inflation pressure-mediated lung injury), volutrauma (overdistension-mediated lung injury), and stress on epithelial cells in the alveoli and/or small airways (atelectrauma), causing activation of inflammatory cells and other cell types, and release of proinflammatory and profibrotic mediators (biotrauma).

The term "mechanical injury to the lungs" includes the act of coughing in patients diagnosed with pulmonary fibrosis conditions including ILDs, IIPs, IPF, NSIP, sarcoidosis, CT-ILD, SSc-ILD, RA-ILD, pleural fibrosis or bronchiolitis obliterans.

Thus, the term "mechanical injury to the lungs" includes the damage to the lung caused by exceeding its physical tolerance in the subset of ILD, IIPs, IPF, NSIP, sarcoidosis, CT-ILD, SSc-ILD, RA-ILD, pleural fibrosis or bronchiolitis obliterans patients, who cough.

The term "mechanical injury to the lungs" includes the damage to the lung caused by exceeding its physical tolerance by mechanical ventilation.

The term 'bronchiolitis obliterans' is interchangeable with the term 'obliterative bronchiolitis' and with the term 'constrictive bronchiolitis' and are intended to have the same meaning herein.

The term coronavirus as used herein refers to human pathogenic coronaviruses including severe acute respiratory syndrome coronavirus (SARS-CoV), Middle East respiratory syndrome coronavirus (MERS-CoV) and SARS-CoV-2.

The coronavirus SARS-CoV and SARS are intended to have the same meaning and are used interchangeably herein.

The coronavirus MERS-CoV and MERS are intended to have the same meaning and are used interchangeably herein.

The coronavirus COVID-19, SARS-CoV-2, and 2019-nCoV are intended to have the same meaning and are used interchangeably herein.

The term 'bronchiolitis obliterans' includes 'bronchiolitis obliterans syndrome' that occurs after lung transplantation or hematopoietic stem cell transplantation (HSCT) or chronic allograft rejection or dysfunction.

The term "acute respiratory failure" refers to the situation when the respiratory system fails in one or both of its gas exchange functions for example oxygenation of and/or elimination of carbon dioxide from mixed venous blood.

The terms 'ventilator-induced lung injury' (VILI) and 'ventilation-induced lung injury' (VILI) and 'ventilator-associated lung injury' and 'ventilation-associated lung injury' (VALI) are intended to have the same meaning and are used interchangeably herein.

The term 'white blood cells' and 'leukocytes' are intended to have the same meaning and are used interchangeably herein.

The term 'monocyte chemoattractant protein-1' (MCP-1) and C-C Motif Chemokine Ligand 2 (CCL-2) are intended to have the same meaning and are used interchangeably herein.

The term "about" or "approximately" means an acceptable error for a particular value as determined by one of ordinary skill in the art, which depends in part on how the value is measured or determined.

In certain embodiments, the term "about" or "approximately" means within one standard deviation. In some embodiments, when no particular margin of error (e.g., a standard deviation to a mean value given in a chart or table of data) is recited, the term "about" or "approximately" means that range which would encompass the recited value and the range which would be included by rounding up or down to the recited value as well, taking into account significant figures. In certain embodiments, the term "about" or "approximately" means within 20%, 15'%, 10% or 5% of the specified value. Whenever the term "about" or "approximately" precedes the first numerical value in a series of two or more numerical values or in a series of two or more ranges of numerical values, the term "about" or "approximately"

applies to each one of the numerical values in that series of numerical values or in that series of ranges of numerical values.

The term 'proinflammatory and profibrotic mediators following mechanical injury to the lungs' means the release of proinflammatory and profibrotic mediators involved in the pathogenesis of pulmonary fibrosis conditions. Proinflammatory mediators such as cytokines and chemokines are released initially at the site of mechanical injury to the lung tissue. These proinflammatory mediators contribute to innate and adaptive immune responses by activating local resident and infiltrating immune cells and other cell types to release and upregulate additional proinflammatory mediators. Together these have a stimulatory effect on fibroblasts which respond by proliferating and differentiating to myofibroblasts, and expressing profibrotic mediators such as the growth factor TGFβ and extracellular matrix proteins (ECMs), leading to extracellular matrix deposition and, in susceptible individuals to the development or progression of a pulmonary fibrosis condition.

The term "medical conditions" (or "conditions" for short) encompasses disorders and diseases.

The term "combination" as used herein refers to either a fixed combination in one dosage unit form, or non-fixed combination.

The term "fixed combination" means that the active ingredients, e.g. a compound of formula (I)-(IX) or pharmaceutically acceptable salt thereof and a combination partner, are both administered to a patient simultaneously in the form of a single entity or dosage The term "non-fixed combination" means that the active ingredients, e.g. a compound (I)-(IX) or pharmaceutically acceptable salt thereof and a combination partner, (e.g. another drug as explained below, also referred to as "therapeutic agent" or "co-agent") are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

The terms "co-administration" or "combined administration" or the like as utilized herein are meant to encompass administration of the compound (I) and the selected combination partner to a single subject in need thereof (e.g. a patient), and are intended to include treatment regimens in which the agents are not necessarily administered by the same route of administration or at the same time.

The term "prodrug" is meant a compound that, after administration, is converted within the body into a pharmacologically active drug.

The term "metabolites" means the intermediates or end products of metabolism, formed as part of the natural biochemical process of degrading and eliminating the compounds.

Pulmonary Fibrosis Conditions

Pulmonary fibrosis conditions according to the invention include but are not limited to:
1. Interstitial lung diseases (ILDs) including:
    Idiopathic interstitial pneumonias (IIPs) such as idiopathic pulmonary fibrosis (IPF), non-specific interstitial pneumonia (NSIP) (may be idiopathic non-specific interstitial pneumonia or secondary to connective tissue disease), respiratory bronchiolitis associated ILD, desquamative interstitial pneumonia, acute interstitial pneumonia, cryptogenic organizing pneumonia (previously called bronchiolitis obliterans with organizing pneumonia), idiopathic lymphoid interstitial pneumonia, combined pulmonary fibrosis and emphysema syndrome, hypersensitivity pneumonitis;
    ILDs associated with systemic diseases for example:
        ILDs associated with connective tissue/autoimmune diseases (connective tissue associated-ILD [CT-ILD]) such as juvenile dermatomyositis, polymyositis, anti-synthetase syndrome, Sjögren's syndrome, systemic sclerosis associated ILD (also called systemic scleroderma) (SSc-ILD), rheumatoid arthritis associated ILD (RA-ILD) or systemic lupus erythematosus;
        ILDs associated with granulomatous diseases such as sarcoidosis or Wegener's granulomatosis;
        ILDS associated with metabolic diseases such as Hermansky-Pudlak syndrome with pulmonary fibrosis and familial hypocalciuric hypercalcaemia;
        ILDs associated with systemic vasculitides such as pulmonary vasculitis;
        Secondary pulmonary hemosiderosis.
    Rare lung diseases for example: pulmonary alveolar proteinosis, pulmonary histiocytosis, pulmonary eosinophilia, idiopathic pulmonary hemosiderosis, idiopathic lymphoid interstitial pneumonia, idiopathic pleuroparenchymal fibroelastosis, or pulmonary alveolar microlithiasis;
    Environmental and occupational diseases that are due to hypersensitivity for example: pneumoconiosis such as, extrinsic allergic alveolitis, asbestosis, silicosis, and due to coal dust, beryllium, hard metal dust exposure, and extrinsic allergic alveolitis for example 'bird fancier's' lung, radiation fibrosis syndrome, or due to exposure to bacteria, molds such as with mycoplasma, pneumoniae and viruses such as due to coronaviruses including COVID-19, SARS or MERS;
    Genetic or inherited diseases for example: familial pulmonary fibrosis (FPF) or familial interstitial pneumonia (FIP);
    Drug induced ILDs (known as DILD or Iatrogenic ILDs), for example with amiodarone, methotrexate or bleomycin;
    ILDs specific to infancy or childhood such as diffuse pulmonary developmental disorders, pulmonary lymphatic dysplasia syndromes, disorders of surfactant metabolism, alveolar or peri-alveolar conditions, pulmonary capillaritis, brain-lung-thyroid syndrome, chronic pneumonitis of infancy, neuroendocrine cell hyperplasia of infancy;
    Unclassifiable idiopathic interstitial pneumonias and unclassifiable ILDs.
2. Pleural fibrosis caused by asbestos-associated diffuse pleural thickening, coronary bypass graft surgery, pleural infection (including tuberculous pleurisy), drug-induced pleuritis, rheumatoid pleurisy, uraemic pleurisy, or hemothorax.
3. Bronchiolitis obliterans which is a type of obstructive lung disease of the small airways, with characteristic features of fibrosis of terminal and distal bronchioles and spirometry showing airflow obstruction. When the cause is either lung transplantation or HSCT or chronic allograft rejection or dysfunction, it is called bronchiolitis obliterans syndrome.

In some embodiments, the pulmonary fibrosis conditions are selected from ILDs, IIPs, IPF, NSIP, sarcoidosis, CT-ILD, SSc-ILD, RA-ILD, pleural fibrosis or bronchiolitis obliterans.

In some embodiments, the pulmonary fibrosis conditions are rare lung diseases selected from pulmonary alveolar proteinosis, pulmonary histiocytosis, pulmonary eosinophilia, idiopathic pulmonary hemosiderosis, idiopathic lymphoid interstitial pneumonia, idiopathic pleuroparenchymal fibroelastosis, or pulmonary alveolar microlithiasis.

In some embodiments, the pulmonary fibrosis conditions are associated with environmental and occupational diseases that are due to hypersensitivity for example: pneumoconiosis such as, extrinsic allergic alveolitis, asbestosis, silicosis, and due to coal dust, beryllium, hard metal dust exposure, and extrinsic allergic alveolitis for example 'bird fancier's' lung, radiation fibrosis syndrome, or due to exposure to bacteria, molds such as with mycoplasma pneumonia or viruses such as due to coronaviruses including COVID-19, SARS or MERS;

In some embodiments, the pulmonary fibrosis conditions are selected from ILDs, IIPs, IPF, NSIP, sarcoidosis, CT-ILD, SSc-ILD, RA-ILD, or are due to coronavirus infection including COVID-19, SARS or MERS, pleural fibrosis or bronchiolitis obliterans.

In some embodiments, the mechanical injury to the lungs is induced by the act of coughing in a subset of patients diagnosed with pulmonary fibrosis conditions who cough.

In some embodiments, the mechanical injury to the lungs is induced by the act of coughing in a subset of patients diagnosed with ILDs, IIPs, IPF, NSIP, sarcoidosis, CT-ILD, SSc-ILD, RA-ILD, pleural fibrosis or bronchiolitis obliterans who cough.

In some embodiments, the mechanical injury to the lungs is induced by mechanical ventilation.

In some embodiments, the pulmonary fibrosis conditions are promoted by mechanical injury to the lungs induced by the act of coughing in a subset of patients diagnosed with pulmonary fibrosis conditions who cough.

In some embodiments, the pulmonary fibrosis conditions are promoted by mechanical injury to the lungs induced by the act of coughing in a subset of patients diagnosed with ILDs, IIPs, IPF, NSIP, sarcoidosis, CT-ILD, SSc-ILD, RA-ILD, pleural fibrosis or bronchiolitis obliterans who cough.

In some embodiments, the pulmonary fibrosis conditions are promoted by mechanical injury to the lungs induced by mechanical ventilation.

In some embodiments, the pulmonary fibrosis conditions are promoted by mechanical injury to the lungs induced by mechanical ventilation of a patient with acute respiratory failure.

In some embodiments, the pulmonary fibrosis conditions promoted by mechanical injury to the lungs induced by mechanical ventilation are selected from ILDs, IIPs, IPF, NSIP, sarcoidosis, CT-ILD, SSc-ILD, RA-ILD, or are due to coronavirus infection including COVID-19, SARS or MERS, or pleural fibrosis or bronchiolitis obliterans.

In some embodiments, the pulmonary fibrosis conditions promoted by mechanical injury to the lungs induced by the act of coughing in a subset of patients diagnosed with ILDs, IIPs, IPF, NSIP, sarcoidosis, CT-ILD, SSc-ILD, RA-ILD, pleural fibrosis or bronchiolitis obliterans who cough, are selected from with ILDs, IIPs, IPF, NSIP, sarcoidosis, CT-ILD, SSc-ILD, RA-ILD, pleural fibrosis or bronchiolitis obliterans.

In a further aspect, this invention provides a method for amelioration of symptoms associated with the release of proinflammatory and profibrotic mediators following mechanical injury to the lungs of patients with pulmonary fibrosis conditions who cough or as a result of mechanical ventilation in patients with either pulmonary fibrosis conditions or acute respiratory failure.

In some embodiments proinflammatory and profibrotic mediators that promote pulmonary fibrosis conditions after mechanical injury to the lungs include cytokines (for example interleukin [IL]-1α/β, IL-6, IL-17A and IL-23), chemokines (for example monocyte chemoattractant protein-1 [MCP-1] also called C-C Motif Chemokine Ligand 2 [CCL-2], C-X-C Motif Chemokine Ligand 1 [CXCL-1] and macrophage inflammatory protein [MIP-2]), growth factors (for example vascular endothelial growth factor [VEGF] and transforming growth factor beta [TGFβ]), mucins (for example Muc5b), extracellular matrix proteins (for example collagen type 1a1 and collagen type 3a1), soluble receptor for advanced glycation endproducts [RAGE], and soluble and membrane-bound intercellular adhesion molecule-1 [ICAM], and Substance P (SP).

Such proinflammatory and profibrotic mediators that promote pulmonary fibrosis conditions after mechanical injury to the lungs are released from various cells including white blood cells (WBCs) such as neutrophils, monocytes (for example Lys6 high inflammation monocytes), macrophages (for example alveolar macrophages), T-cells and mast cells, as well as endothelial cells, epithelial cells, fibroblasts and myofibroblasts.

Neurokinin(NK)-1 Receptor Antagonists

One or more NK-1 receptor antagonists can be used for treating pulmonary fibrosis conditions promoted by mechanical injury to the lungs.

In some embodiments, the NK-1 receptor antagonist is or comprises a selective NK-1 receptor antagonist.

Non-limiting examples of NK-1 receptor antagonists include orvepitant, aprepitant, fosaprepitant, rolapitant, netupitant, fosnetupitant, serlopitant, tradipitant or analogs, derivatives, prodrug, metabolites or pharmaceutically acceptable salts thereof.

Further examples of NK-1 receptor antagonists of use according to the invention include (5R)-5-[5-[{2-[3, 5-bis (trifluoromethyl) phenyl]-2-methylpropanoyl} (methyl) amino]-4-(4-fluoro-2-methylphenyl)-2-pyridinyl]-2-methyl-D-prolinamide or pharmaceutically acceptable salts thereof, having the following chemical structure (A), hereinafter Compound (A);

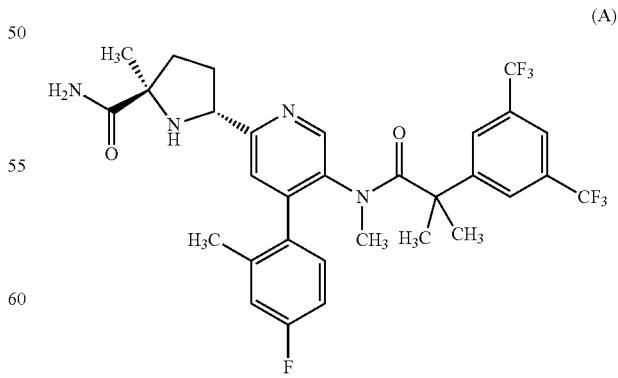

(A)

or 2R,5S,7R)-N$^6$-{(1R)-1-[3,5-bis(trifluoromethyl)phenyl]ethyl}-7-(4-fluoro-2-methylphenyl)-N$^6$-methyl-1,8-diazaspiro[4.5]decane-2,8-dicarboxamide or pharmaceutically acceptable salts thereof, having the following chemical structure (B), hereinafter Compound (B).

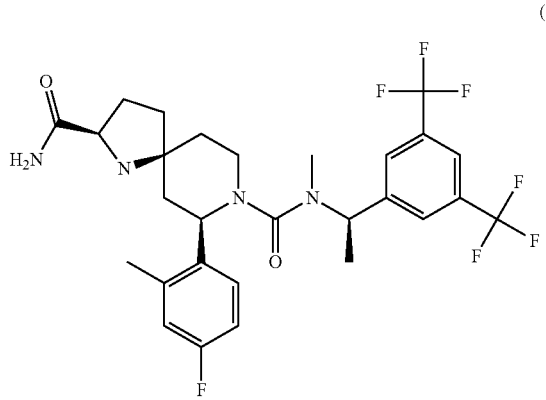

(B)

In some embodiments the subset of patients diagnosed with ILDs, IIPs, IPF, NSIP, sarcoidosis, CT-ILD, SSc-ILD, RA-ILD, pleural fibrosis or bronchiolitis obliterans who cough or patients with pulmonary fibrosis conditions as a result of mechanical ventilation, are treated with an NK-1 receptor antagonist selected from orvepitant, aprepitant, fosaprepitant, rolapitant, netupitant, fosnetupitant, serlopitant, tradipitant, Compound A, Compound B, prodrug, metabolites or pharmaceutically acceptable salts thereof.

In some embodiments, the invention provides a method of treating pulmonary fibrosis conditions promoted by mechanical injury to the lungs to a patient in need of such treatment comprising administering to said patient a therapeutically effective amount of an NK-1 receptor antagonist selected from orvepitant, aprepitant, fosaprepitant, rolapitant, netupitant, fosnetupitant, serlopitant, tradipitant, Compound A, Compound B, prodrug, metabolites or pharmaceutically acceptable salts thereof.

In some embodiments, the invention provides a method of treating pulmonary fibrosis conditions promoted by mechanical injury to the lungs as a result of mechanical ventilation to a patient in need of such treatment comprising administering to said patient a therapeutically effective amount of an NK-1 receptor antagonist selected from orvepitant, aprepitant, fosaprepitant, rolapitant, netupitant, fosnetupitant, serlopitant, tradipitant, Compound A, Compound B, prodrug, metabolites or pharmaceutically acceptable salts thereof.

In some embodiments, the invention provides a method of treating pulmonary fibrosis conditions selected from ILDs, IIPs, IPF, NSIP, sarcoidosis, CT-ILD, SSc-ILD, RA-ILD, or due to coronavirus infection including COVID-19, SARS or MERS, pleural fibrosis or bronchiolitis obliterans promoted by mechanical injury to the lungs as a result of mechanical ventilation to a patient in need of such treatment comprising administering to said patient a therapeutically effective amount of an NK-1 receptor antagonist selected from orvepitant, aprepitant, fosaprepitant, rolapitant, netupitant, fosnetupitant, serlopitant, tradipitant, Compound A, Compound B, prodrug, metabolites or pharmaceutically acceptable salts thereof.

In some embodiments, the invention provides a method of treating pulmonary fibrosis conditions promoted by mechanical injury induced by the act of coughing in a subset of patients diagnosed with ILDs, IIPs, IPF, NSIP, sarcoidosis, CT-ILD, SSc-ILD, RA-ILD, pleural fibrosis or bronchiolitis obliterans who cough comprising administering to said patient a therapeutically effective amount of an NK-1 receptor antagonist selected from orvepitant, aprepitant, fosaprepitant, rolapitant, netupitant, fosnetupitant, serlopitant, tradipitant, Compound A, Compound B, prodrug, metabolites or pharmaceutically acceptable salts thereof.

In some embodiments, the invention provides a method of treating pulmonary fibrosis conditions selected from ILDs, IIPs, IPF, NSIP, sarcoidosis, CT-ILD, SSc-ILD, RA-ILD, pleural fibrosis or bronchiolitis obliterans promoted by mechanical injury induced by the act of coughing in a subset of patients with ILDs, IIPs, IPF, NSIP, sarcoidosis, CT-ILD, SSc-ILD, RA-ILD, pleural fibrosis or bronchiolitis obliterans who cough comprising administering to said patient a therapeutically effective amount of an NK-1 receptor antagonist selected from orvepitant, aprepitant, fosaprepitant, rolapitant, netupitant, fosnetupitant, serlopitant, tradipitant, Compound A, Compound B, prodrug, metabolites or pharmaceutically acceptable salts thereof.

In some embodiments, the invention provides a method of treating pulmonary fibrosis conditions promoted by mechanical injury to the lungs as results of mechanical ventilation of a patient with acute respiratory failure, comprising administering to said patient a therapeutically effective amount of an NK-1 receptor antagonist selected from orvepitant, aprepitant, fosaprepitant, rolapitant, netupitant, fosnetupitant, serlopitant, tradipitant, Compound A, Compound B, prodrug, metabolites or pharmaceutically acceptable salts thereof.

In certain embodiments, the NK-1 receptor antagonist is or comprises orvepitant or a pharmaceutically acceptable salt, solvate, hydrate, or metabolite thereof.

Chemically, the generic name orvepitant refers to Compound (I).

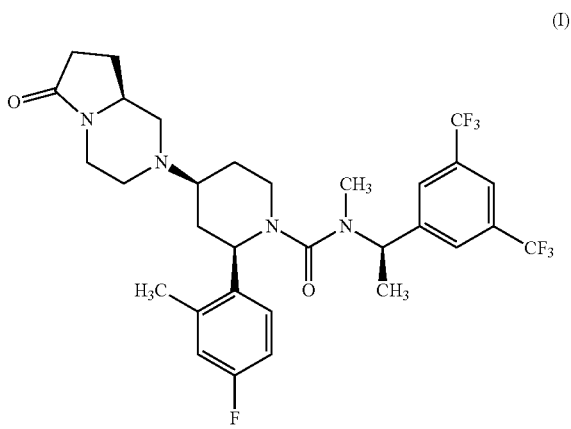 [SMILES: Cc1cc(F)ccc1[C@H]1C[C@@H](N2CCN3C(=O)CC[C@H]3C2)CCN1C(=O)N(C)[C@H](C)c1cc(C(F)(F)F)cc(C(F)(F)F)c1]

(I)

The compound (I) or its pharmaceutically acceptable salts may be prepared by the processes described in PCT Publication Nos. WO2003/066635, WO2009/124996, WO2007/048642 and WO2017/118584 which are incorporated herein by reference.

Specifically, the Examples 9a and 11 of WO2003/066635 describe the synthesis of the compound (I) as free base and as hydrochloride salt respectively. Specific crystalline forms of hydrochloride salt namely anhydrous and dihydrate crystalline forms are described in the Examples 11a and 11b respectively. Example 11c describes the synthesis of the compound (I) as a maleate salt. Examples 2-8 of WO2009/

124996 describe the synthesis of the maleate salt of the compound (I) as anhydrous crystalline form (Form1).

Orvepitant maleate Form 1 is characterized by X-ray powder diffraction (XRD) pattern expressed in terms of 2 theta angles and obtained with a diffractometer using copper KaX-radiation, wherein the XRD pattern comprises 2 theta angle peaks at essentially at 7.3±0.1, 7.5±0.1, 10.9±0.1, 12.7±0.1, 16.5±0.1 degrees, which correspond respectively to d-spacings at 12.2, 11.8, 8.1, 7.0 and 5.4 Angstroms (Å).

Example 1 of WO2007/048642 discloses a process for preparing an intermediate in the synthesis of the compound (I).

In some embodiments the compound for use according to the present invention is or comprise orvepitant or pharmaceutical acceptable salt thereof.

In some embodiments the compound for use according to the present invention is or comprise orvepitant maleate.

In other embodiments the compound for use according to the present invention is or comprise orvepitant maleate as anhydrous crystalline form.

In further embodiments the compound for use according to the present invention is or comprise maleate as anhydrous crystalline Form 1.

In some embodiments, the invention provides a method of treating pulmonary fibrosis conditions promoted by mechanical injury to the lungs to a patient in need of such treatment comprising administering to said patient a therapeutically effective amount of orvepitant or pharmaceutically acceptable salts thereof.

In some embodiments, the invention provides a method of treating pulmonary fibrosis conditions promoted by mechanical injury to the lungs to a patient in need of such treatment comprising administering to said patient a therapeutically effective amount of orvepitant maleate.

In some embodiments, the invention provides a method of treating pulmonary fibrosis conditions promoted by mechanical injury to the lungs to a patient in need of such treatment comprising administering to said patient a therapeutically effective amount of orvepitant maleate as anhydrous crystalline form.

In some embodiments, the invention provides a method of treating pulmonary fibrosis conditions promoted by mechanical injury to the lungs to a patient in need of such treatment comprising administering to said patient a therapeutically effective amount of orvepitant maleate as anhydrous crystalline Form 1.

In some embodiments, the invention provides a method of treating pulmonary fibrosis conditions promoted by mechanical injury to the lungs as a result of mechanical ventilation to a patient in need of such treatment comprising administering to said patient a therapeutically effective amount of orvepitant or pharmaceutically acceptable salts thereof.

In some embodiments, the invention provides a method of treating pulmonary fibrosis conditions promoted by mechanical injury to the lungs as a result of mechanical ventilation to a patient in need of such treatment comprising administering to said patient a therapeutically effective amount of orvepitant maleate.

In some embodiments, the invention provides a method of treating pulmonary fibrosis conditions promoted by mechanical injury to the lungs as a result of mechanical ventilation to a patient in need of such treatment comprising administering to said patient a therapeutically effective amount of orvepitant maleate as anhydrous crystalline form.

In some embodiments, the invention provides a method of treating pulmonary fibrosis conditions promoted by mechanical injury to the lungs as a result of mechanical ventilation to a patient in need of such treatment comprising administering to said patient a therapeutically effective amount of orvepitant maleate as anhydrous crystalline Form 1.

In some embodiments, the invention provides a method of treating pulmonary fibrosis conditions promoted by mechanical injury to the lungs as a result of mechanical ventilation of a patient with acute respiratory failure, comprising administering to said patient a therapeutically effective amount of orvepitant or pharmaceutically acceptable salts thereof.

In some embodiments, the invention provides a method of treating pulmonary fibrosis conditions promoted by mechanical injury to the lungs as a result of mechanical ventilation of a patient with acute respiratory failure, comprising administering to said patient a therapeutically effective amount of orvepitant maleate.

In some embodiments, the invention provides a method of treating pulmonary fibrosis conditions promoted by mechanical injury to the lungs as a result of mechanical ventilation of a patient with acute respiratory failure, comprising administering to said patient a therapeutically effective amount of orvepitant maleate as anhydrous crystalline form.

In some embodiments, the invention provides a method of treating pulmonary fibrosis conditions promoted by mechanical injury to the lungs as a result of mechanical ventilation of a patient with acute respiratory failure, comprising administering to said patient a therapeutically effective amount of orvepitant maleate as anhydrous crystalline Form 1.

In some embodiments, the invention provides a method of treating pulmonary fibrosis conditions selected from ILDs, IIPs, IPF, NSIP, sarcoidosis, CT-ILD, SSc-ILD, RA-ILD, or due to coronavirus infection including COVID-19, SARS or MERS, pleural fibrosis, or bronchiolitis obliterans promoted by mechanical injury to the lungs as a results of mechanical ventilation to a patient with ILDs, IIPs, IPF, NSIP, sarcoidosis, CT-ILD, SSc-ILD, RA-ILD, coronavirus infection including COVID-19, SARS or MERS, pleural fibrosis, or bronchiolitis obliterans comprising administering to said patient a therapeutically effective amount of orvepitant or pharmaceutically acceptable salts thereof.

In some embodiments, the invention provides a method of treating pulmonary fibrosis conditions selected from ILDs, IIPs, IPF, NSIP, sarcoidosis, CT-ILD, SSc-ILD, RA-ILD, or due to coronavirus infection including COVID-19, SARS or MERS, pleural fibrosis, bronchiolitis obliterans promoted by mechanical injury to the lungs as a result of mechanical ventilation to a patient with ILDs, IIPs, IPF, NSIP, sarcoidosis, CT-ILD, SSc-ILD, RA-ILD, coronavirus infection including COVID-19, SARS or MERS, pleural fibrosis, or bronchiolitis obliterans comprising administering to said patient a therapeutically effective amount of orvepitant maleate.

In some embodiments, the invention provides a method of treating pulmonary fibrosis conditions selected from ILDs, IIPs, IPF, NSIP, sarcoidosis, CT-ILD, SSc-ILD, RA-ILD, or due to coronavirus infection including COVID-19, SARS or MERS, pleural fibrosis, bronchiolitis obliterans promoted by mechanical injury to the lungs as a result of mechanical ventilation to a patient with ILDs, IIPs, IPF, NSIP, sarcoidosis, CT-ILD, SSc-ILD, RA-ILD, coronavirus infection including COVID-19, SARS or MERS, pleural fibrosis or bronchiolitis obliterans comprising administering to said patient a therapeutically effective amount of orvepitant maleate as anhydrous crystalline form.

In some embodiments, the invention provides a method of treating pulmonary fibrosis conditions selected from ILDs, IIPs, IPF, NSIP, sarcoidosis, CT-ILD, SSc-ILD, RA-ILD, or due to coronavirus infection including COVID-19, SARS or MERS, pleural fibrosis, or bronchiolitis obliterans promoted by mechanical injury to the lungs as a result of mechanical ventilation to a patient with ILDs, IIPs, IPF, NSIP, sarcoidosis, CT-ILD, SSc-ILD, RA-ILD, coronavirus infection including COVID-19, SARS or MERS, pleural fibrosis, or bronchiolitis obliterans as a result of mechanical ventilation comprising administering to said patient a therapeutically effective amount of orvepitant maleate as anhydrous crystalline Form 1.

In some embodiments, the invention provides a method of treating pulmonary fibrosis conditions promoted by mechanical injury to the lungs induced by the act of coughing in a subset of patients with ILDs, IIPs, IPF, NSIP, sarcoidosis, CT-ILD, SSc-ILD, RA-ILD, pleural fibrosis or bronchiolitis obliterans who cough comprising administering to said patient a therapeutically effective amount of orvepitant or pharmaceutically acceptable salts thereof.

In some embodiments, the invention provides a method of treating pulmonary fibrosis conditions promoted by mechanical injury to the lungs induced by the act of coughing in a subset of patients with ILDs, IIPs, IPF, NSIP, sarcoidosis, CT-ILD, SSc-ILD, RA-ILD, pleural fibrosis or bronchiolitis obliterans who cough comprising administering to said patient a therapeutically effective amount of orvepitant maleate.

In some embodiments, the invention provides a method of treating pulmonary fibrosis conditions promoted by mechanical injury to the lungs induced by the act of coughing in a subset of patients with ILDs, IIPs, IPF, NSIP, sarcoidosis, CT-ILD, SSc-ILD, RA-ILD, pleural fibrosis or bronchiolitis obliterans who cough comprising administering to said patient a therapeutically effective amount of orvepitant maleate as anhydrous crystalline form.

In some embodiments, the invention provides a method of treating pulmonary fibrosis conditions promoted by mechanical injury to the lungs induced by the act of coughing in a subset of patients with ILDs, IIPs, IPF, NSIP, sarcoidosis, CT-ILD, SSc-ILD, RA-ILD, pleural fibrosis or bronchiolitis obliterans who cough comprising administering to said patient a therapeutically effective amount of orvepitant maleate as anhydrous crystalline Form 1.

In some embodiments, the invention provides a method of treating pulmonary fibrosis conditions selected from ILDs, IIPs, IPF, NSIP, sarcoidosis, CT-ILD, SSc-ILD, RA-ILD, pleural fibrosis or bronchiolitis obliterans promoted by mechanical injury to the lungs induced by the act of coughing in a subset of patients with ILDs, IIPs, IPF, NSIP, sarcoidosis, CT-ILD, SSc-ILD, RA-ILD, pleural fibrosis or bronchiolitis obliterans who cough comprising administering to said patient a therapeutically effective amount of orvepitant or pharmaceutically acceptable salts thereof.

In some embodiments, the invention provides a method of treating pulmonary fibrosis conditions selected from ILDs, IIPs, IPF, NSIP, sarcoidosis, CT-ILD, SSc-ILD, RA-ILD, pleural fibrosis or bronchiolitis obliterans promoted by mechanical injury to the lungs induced by the act of coughing in a subset of patients with ILDs, IIPs, IPF, NSIP, sarcoidosis, CT-ILD, SSc-ILD, RA-ILD, pleural fibrosis or bronchiolitis obliterans who cough comprising administering to said patient a therapeutically effective amount of orvepitant maleate.

In some embodiments, the invention provides a method of treating pulmonary fibrosis conditions selected from ILDs, IIPs, IPF, NSIP, sarcoidosis, CT-ILD, SSc-ILD, RA-ILD, pleural fibrosis or bronchiolitis obliterans promoted by mechanical injury to the lungs induced by the act of coughing in a subset of patients with ILDs, IIPs, IPF, NSIP, sarcoidosis, CT-ILD, SSc-ILD, RA-ILD, pleural fibrosis or bronchiolitis obliterans who cough comprising administering to said patient a therapeutically effective amount of orvepitant maleate as anhydrous crystalline form.

In some embodiments, the invention provides a method of treating pulmonary fibrosis conditions selected from ILDs, IIPs, IPF, NSIP, sarcoidosis, CT-ILD, SSc-ILD, RA-ILD, pleural fibrosis or bronchiolitis obliterans promoted by mechanical injury to the lungs induced by the act of coughing in a subset of patients ILDs, IIPs, IPF, NSIP, sarcoidosis, CT-ILD, SSc-ILD, RA-ILD, pleural fibrosis or bronchiolitis obliterans who cough comprising administering to said patient a therapeutically effective amount of orvepitant maleate as anhydrous crystalline Form 1.

In additional embodiments, the NK-1 receptor antagonist is or includes aprepitant or fosaprepitant (a prodrug of aprepitant) or a pharmaceutically acceptable salt, solvate, hydrate, clathrate, polymorph prodrug or metabolite thereof.

Chemically the generic name of aprepitant refers to Compound (II).

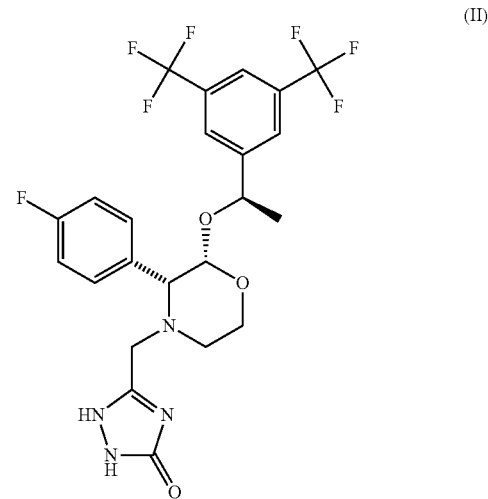 [SMILES: C[C@@H](O[C@@H]1OCCN(Cc2nc(=O)[nH][nH]2)[C@@H]1c1ccc(F)cc1)c1cc(C(F)(F)F)cc(C(F)(F)F)c1]

(II)

The compound (II) or its pharmaceutically acceptable salts may be prepared by the processes described in PCT Publication No. WO94/00440 and WO95/16679 which are incorporated herein by reference. Specifically, Example 75 of PCT Publication No. WO95/16679 describes the synthesis of compound (II).

Polymorphic forms of compound of formula (II) may be prepared by the processes described in U.S. Pat. No. 6,096,742 which is also incorporated herein by reference.

Specifically, a polymorphic forms of the compound (II) characterized by an X-ray powder diffraction pattern comprising 2 theta angle peaks at essentially at 12.0, 15.3, 16.6, 17.0, 17.6, 19.4, 20.0, 21.9, 23.6, 23.8 is described in U.S. Pat. No. 6,096,742.

In some embodiments, the compound for use according to the present invention is or comprise aprepitant or a pharmaceutically acceptable salt thereof.

In some embodiments, the compound for use according to the present invention is or comprise aprepitant as a crystalline form.

Chemically, the generic name of fosaprepitant refers to compound of formula (III).

Chemically the generic name of netupitant refers to Compound (V).

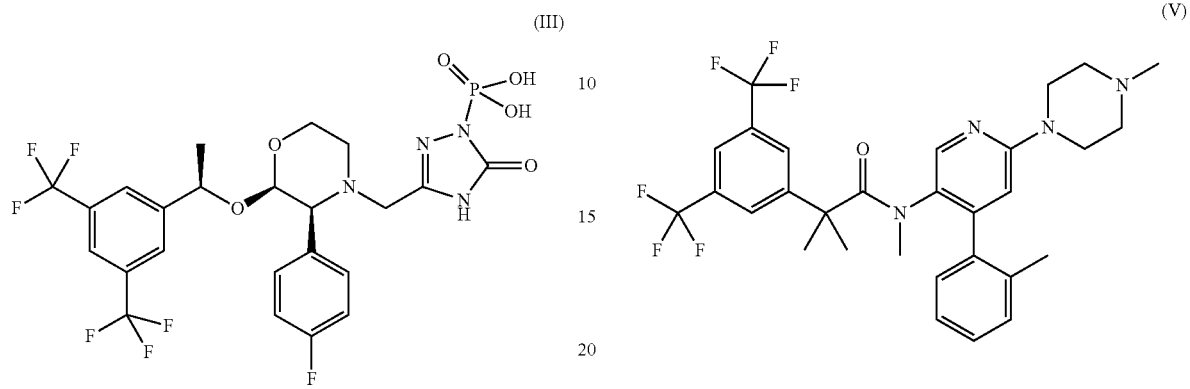

The compound (III) and pharmaceutically acceptable salts, including its dimeglumine salt, can be prepared by the process described in U.S. Pat. No. 5,691,336 and PCT Publication Nos. WO2010/018595 and WO2011104581, which are incorporated herein by reference.

In additional embodiments, the compound for use according to the present invention is fosaprepitant or pharmaceutically acceptable salts thereof.

In further embodiments, the compound for use according to the present invention is fosaprepitant dimeglumine.

In yet further embodiments, the NK-1 receptor antagonist is or includes rolapitant or a pharmaceutically acceptable salt, solvate, hydrate, polymorph, produg or metabolite thereof.

Chemically, the generic name of rolapitant refers to Compound (IV).

The compound (V) or its pharmaceutically acceptable salts may be prepared by the processes described in U.S. Pat. No. 6,297,375 and PCT Publication No. WO2015/171489, which are herein incorporated by reference.

In other embodiments, the NK-1 receptor antagonist is or includes fosnetupitant (prodrug of netupitant) a pharmaceutically acceptable salt, solvate, hydrate, clathrate, polymorph, or metabolite thereof.

Chemically, the generic name of fosnetupitant refers to Compound (VI).

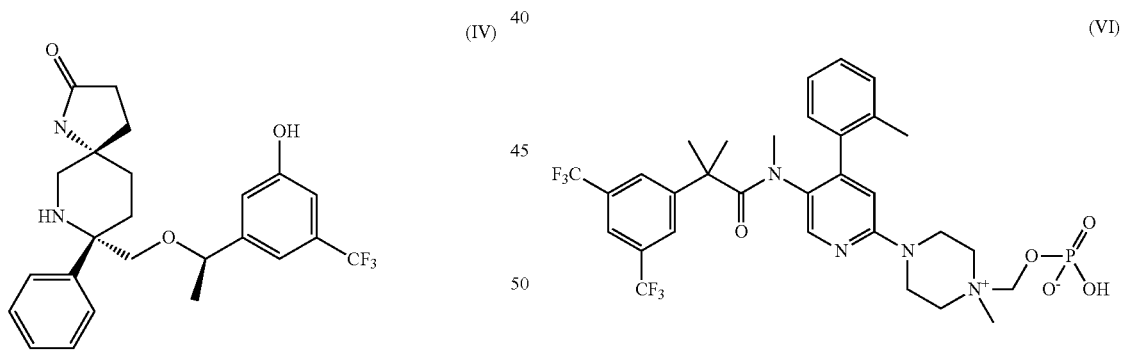

The compound (IV) or its pharmaceutically acceptable salts may be prepared by the processes described in U.S. Pat. No. 7,049,320 (the '320 patent), U.S. Patent No. 2007/0244142 and PCT Publication No. WO2005/063243, which are herein incorporated by reference.

Process for preparing pharmaceutical compositions for intravenous administration of compound (IV) or pharmaceutically acceptable salts, hydrates or prodrugs are described in U.S. Pat. No. 9,101,615, which is also incorporated by reference.

In still further embodiments, the NK-1 receptor antagonist is or includes netupitant or a pharmaceutically acceptable salt, solvate, hydrate, polymorph, prodrug or metabolite thereof.

The compound (VI) or its pharmaceutically acceptable salts, including the hydrochloride salt, may be prepared by the processes described in U.S. Pat. No. 10,208,073, which is incorporated herein by reference.

In further embodiments the compound for use according to the present invention is fosnetupitant hydrochloride.

In yet other embodiments the NK-1 receptor antagonist is or includes serlopitant, or a pharmaceutically acceptable salt, solvate, hydrate, clathrate, polymorph. prodrug or metabolite thereof.

Chemically, the generic name of serlopitant refers to Compound (VII).

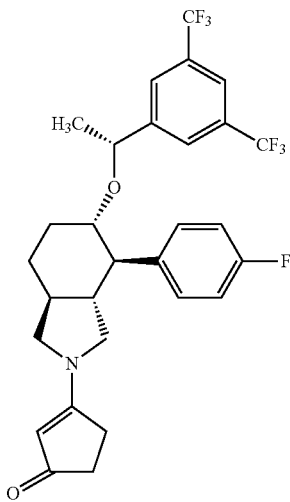

The compound (VII) or its pharmaceutically acceptable salts may be prepared by the processes described in U.S. Pat. No. 7,217,731 and in PCT Publication No. WO08054690, which are incorporated herein by reference.

In still other embodiments, the NK-1 receptor antagonist is or includes tradipitant, or a pharmaceutically acceptable salt, solvate, hydrate, polymorph, prodrug or metabolite thereof.

Chemically, the generic name of tradipitant refers to Compound (IX).

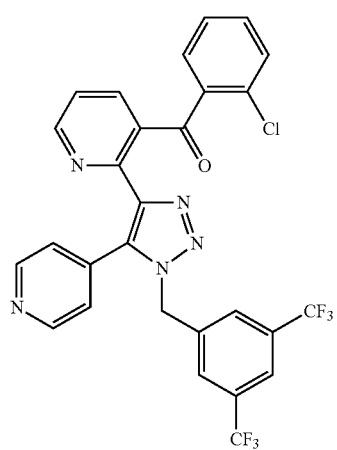

The compound (IX) or its pharmaceutically acceptable salts may be prepared by the processes described in U.S. Pat. No. 7,320,994, which is incorporated herein by reference.

In still other embodiments, the NK-1 receptor antagonist is or includes Compound A.

Compound A, pharmaceutically acceptable salts or anhydrous crystalline forms thereof may be prepared by the processes described in International Patent publication No. WO2009138393, which is incorporated herein by reference.

In still other embodiments, the NK-1 receptor antagonist is or includes Compound B.

Compound B, pharmaceutically acceptable salts or anhydrous crystalline forms thereof may be prepared by the processes described in International Patent publication No. WO 2009133135, which is incorporated herein by reference.

Pharmaceutical Compositions

In another aspect, the invention provides a pharmaceutical composition comprising an NK-1 receptor antagonist and one or more pharmaceutically acceptable carriers or excipients for use in treating mechanical injury to the lungs in both the subset of patients with pulmonary fibrosis conditions who cough and patients with a pulmonary fibrosis condition as a result of mechanical ventilation.

In certain embodiments, the NK-1 receptor antagonist is selected from orvepitant, aprepitant, fosaprepitant, rolapitant, netupitant, fosnetupitant, serlopitant, Compound A, Compound B, or a pharmaceutically acceptable salt, solvate, hydrate, polymorph, prodrug or metabolite thereof.

In some embodiments, the invention provides a method of treating pulmonary fibrosis conditions in both the subset of patients with pulmonary fibrosis conditions who cough or patients with a pulmonary fibrosis condition as a result of mechanical ventilation, by treating a patient in need of such treatment comprising administering to said patient a therapeutically effective amount of an NK-1 receptor antagonist selected from orvepitant, aprepitant, fosaprepitant, rolapitant, netupitant, fosnetupitant, serlopitant, tradipitant, Compound A, Compound B, or prodrug, metabolites or pharmaceutically acceptable salts thereof, and one or more pharmaceutically acceptable carriers or excipients.

In some embodiments, the invention provides a method of treating pulmonary fibrosis conditions promoted by mechanical injury to the lungs as a result of mechanical ventilation to a patient in need of such treatment comprising administering to said patient a therapeutically effective amount of an neurokinin-1 receptor antagonist selected from orvepitant, aprepitant, fosaprepitant, rolapitant, netupitant, fosnetupitant, serlopitant, tradipitant, Compound A, Compound B, or prodrug, metabolites or pharmaceutically acceptable salt thereof and one or more pharmaceutically acceptable carriers or excipients.

In some embodiments, the invention provides a method of treating pulmonary fibrosis conditions promoted by mechanical injury to the lungs induced by the act of coughing in a subset of patients diagnosed with ILDs, IIPs, IPF, NSIP, sarcoidosis, CT-ILD, SSc-ILD, RA-ILD, pleural fibrosis or bronchiolitis obliterans who cough comprising administering to said patient a therapeutically effective amount of an NK-1 receptor antagonist selected from orvepitant, aprepitant, fosaprepitant, rolapitant, netupitant, fosnetupitant, serlopitant, tradipitant, Compound A, Compound B, or prodrug, metabolites or pharmaceutically acceptable salt thereof and one or more pharmaceutically acceptable carriers or excipients.

In some embodiments, the invention provides a method of treating pulmonary fibrosis conditions selected from ILDs, IIPs, IPF, NSIP, sarcoidosis, CT-ILD, SSc-ILD, RA-ILD, pleural fibrosis or bronchiolitis obliterans promoted by mechanical injury to the lungs induced by the act of coughing in a subset of patients diagnosed with ILDs, IIPs, IPF, NSIP, sarcoidosis, CT-ILD, SSc-ILD, RA-ILD, pleural fibrosis or bronchiolitis obliterans who cough comprising administering to said patient a therapeutically effective amount of an NK-1 receptor antagonist selected from orvepitant, aprepitant, fosaprepitant, rolapitant, netupitant, fosnetupitant, serlopitant, tradipitant, Compound A, Compound B, or prodrug, metabolites or pharmaceutically acceptable salt thereof and one or more pharmaceutically acceptable carriers or excipients.

In some embodiments, the invention provides a method of treating pulmonary fibrosis conditions selected from ILDs, IIPs, IPF, NSIP, sarcoidosis, CT-ILD, SSc-ILD, RA-ILD, or due to coronavirus infection including COVID-19, SARS or MERS, or pleural fibrosis or bronchiolitis obliterans promoted by mechanical injury to the lungs as a result of mechanical ventilation, to a patient with ILDs, IIPs, IPF, NSIP, sarcoidosis, CT-ILD, SSc-ILD, RA-ILD, coronavirus infection including COVID-19, SARS or MERS, or pleural fibrosis or bronchiolitis obliterans comprising administering to said patient a therapeutically effective amount of an NK-1 receptor antagonist selected from orvepitant, aprepitant, fosaprepitant, rolapitant, netupitant, fosnetupitant, serlopitant, tradipitant, Compound A, Compound B, or prodrug, metabolites or pharmaceutically acceptable salt thereof and one or more pharmaceutically acceptable carriers or excipients.

In some embodiments, the invention provides a method of treating pulmonary fibrosis conditions promoted by mechanical injury to the lungs as results of mechanical ventilation of a patient with acute respiratory failure, comprising administering to said patient a therapeutically effective amount of an neurokinin-1 receptor antagonist selected from orvepitant, aprepitant, fosaprepitant, rolapitant, netupitant, fosnetupitant, serlopitant, tradipitant, Compound A, Compound B, prodrug, metabolites or pharmaceutically acceptable salts thereof and thereof and one or more pharmaceutically acceptable carriers or excipients.

In additional embodiments, the NK-1 receptor antagonist is orvepitant or a pharmaceutically acceptable salt, solvate, hydrate, polymorph, prodrug or metabolite thereof.

In further embodiments, the NK-1 receptor antagonist is orvepitant maleate.

In still further embodiments, the NK-1 receptor antagonist is orvepitant maleate anhydrous crystalline form (Form1).

Pharmaceutical compositions for use in accordance with the present invention may be formulated in a conventional manner for use in human and veterinary medicine using one or more pharmaceutically acceptable carriers or excipients.

Thus, the NK-1 receptor antagonist (e.g., orvepitant) can be administered via any suitable route including oral, buccal, sub-lingual, parenteral (including intramuscular, subcutaneous, intradermal intravascular, intravenous, intraarterial, intramedullary and intrathecal), topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycolate or croscarmellose sodium); or wetting agents (e.g. sodium lauryl sulphate).

The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal or sub-lingual administration the composition may take the form of tablets or wafers formulated in conventional manner.

The NK-1 receptor antagonist (e.g., orvepitant) may be formulated for parenteral administration by bolus injection or continuous infusion. Formulations for injection may be presented in unit dosage form e.g. in ampoules or in multidose containers, with/or without an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The NK-1 receptor antagonist (e.g., orvepitant) can be formulated for dermal administration.

Dermal administration may include topical application or transdermal administration. Transdermal application can be accomplished by suitable patches, emulsions, ointments, solutions, suspensions, pastes, foams, aerosols, lotions, creams or gels as is generally known in the art, specifically designed for the transdermal delivery of active agents, optionally in the presence of specific permeability enhancers. Topical compositions can likewise take one or more of these forms. One or more active compounds may be present in association with one or more non-toxic pharmaceutically acceptable auxiliaries such as excipients, adjuvants (e.g. buffers), carriers, inert solid diluents, suspending agents, preservatives, fillers, stabilizers, anti-oxidants, food additives, bioavailability enhancers, coating materials, granulating and disintegrating agents, binding agents etc., and, if desired, other active ingredients.

The pharmaceutical composition may be formulated, for example, for immediate release, sustained release, pulsed release, two or more step release, or depot or any other kind of release.

The manufacture of the pharmaceutical compositions according to the present subject matter may be performed according to methods known in the art and will be explained in further detail below. Commonly known and used pharmaceutically acceptable auxiliaries as well as further suitable diluents, flavourings, sweetening agents, colouring agents etc. may be used, depending on the intended mode of administration as well as particular characteristics of the active compound to be used, such as solubility, bioavailability etc.

Any non-toxic, inert, and effective topical, oral, etc. pharmaceutically acceptable carrier may be used to formulate the compositions described herein. Well-known carriers used to formulate other topical therapeutic compositions for administration to humans are useful in these compositions. Examples of these components that are well known to those of skill in the art are described in The Merck Index, Thirteenth Edition, Budavari et al., Eds., Merck & Co., Inc., Rahway, N.J. (2001); the CTFA (Cosmetic, Toiletry, and Fragrance Association) *International Cosmetic Ingredient Dictionary and Handbook*, Tenth Edition (2004); and the "Inactive Ingredient Guide", U.S. Food and Drug Administration (FDA) Center for Drug Evaluation and Research (CDER) Office of Management, January 1996, the contents of which are hereby incorporated by reference in their entirety. Examples of such useful cosmetically acceptable excipients, carriers and diluents include distilled water, physiological saline, Ringer's solution, dextrose solution, Hank's solution, and DMSO, which are among those suitable for use herein.

These additional other inactive components, as well as effective formulations and administration procedures, are well known in the art and are described in standard textbooks, such as *Goodman and Gillman's: The Pharmacological Bases of Therapeutics,* 8th Ed., Gilman et al. Eds. Pergamon Press (1990) and Remington's Pharmaceutical Sciences, 17th Ed., Mack Publishing Co., Easton, Pa. (1990), both of which are incorporated by reference herein in their entirety.

In certain embodiments, the present topical compositions are formulated in a serum, a gel cream, a lotion, a cream, an ointment, a gel, an aerosol, a foam, a foamable liquid, a solution (solubilized system), a paste, a suspension, a dispersion, an emulsion, a skin cleanser, a milk, a mask, a solid stick, a bar (such as a soap bar), an encapsulated formulation, a microencapsulated formulation, microspheres or nanospheres or vesicular dispersions, or other cosmetically acceptable topical dosage form. In the case of vesicular dispersions, the vesicles may be composed of lipids, which can be of the ionic or nonionic type, or a mixture thereof.

The formulation can comprise one or more of an aqueous formulation and/or an anhydrous formulation.

In certain embodiments, the NK-1 receptor antagonist (e.g., orvepitant) is administered orally (e.g., as a capsule or tablet, optionally with an enteric coating).

In other embodiments, the NK-1 receptor antagonist (e.g., orvepitant) is administered parenterally (e.g., intravenously, subcutaneously or intradermally).

For the treatment of medical conditions of the present invention described herein, in some embodiments the NK-1 receptor antagonist (e.g., orvepitant) is administered in a dose of about 0.5 to 60 mg (e.g., per day or per dose) which can be administered in a single dose or in divided doses. Preferably, it is 1 to 60 mg, more preferably 2.5 to 60 mg, more preferably 10 to 60 mg, more preferably 10 to 40 mg, more preferably 20 to 40 mg, more preferably 10 to 30 mg, more preferably 25 to 35 mg.

In certain embodiments, the NK-1 receptor antagonist (e.g., orvepitant) is administered in a dose of about 10 mg, about 15 mg, about 20 mg, about 25 mg, about 26 mg, about 27 g, about 28 mg, about 29 mg, about 30 mg, about 31 mg, about 32 mg, about 33 mg, about 34 mg, about 35 mg, about 40 mg, about 45 mg, about 50 mg, about 55 mg, or about 60 mg one or more times a day.

In some embodiments, the therapeutically effective dose of the NK-1 antagonist (e.g., orvepitant) is administered one or more (e.g., two) times a day, or once every two or three days, or once, twice or thrice a week.

In some embodiments, a therapeutically effective amount of the NK-1 antagonist (e.g., orvepitant) is administered over a period of at least 1 week, 2 weeks, 3 weeks, 1 month, 1.5 months, 2 months, 3 months, 4 months, 5 months, 6 months, 12 months, 18 months, 24 months, or 36 months, or longer.

In another aspect, this invention provides a method of treating pulmonary fibrosis conditions promoted by mechanical injury to the lungs, wherein an NK-1 antagonist (e.g., orvepitant) or a pharmaceutically acceptable salt, solvate or polymorph thereof is administered to a patient in need of such treatment according to a schedule, wherein a least one loading dose is first administered, and second, at least one therapeutically effect maintenance dose is administered.

In one embodiment, the loading dose is five times, four times, three times, or two or one and a half times the maintenance dose. In a further embodiment, the loading dose is administered from day 1 up to day 2, and the maintenance dose is administered on day 3 and thereafter.

In one embodiment, the loading dose is five times, four times, three times, or two or one and a half times the maintenance dose. In a further embodiment, the loading dose is administered from day 1 up to day 3, and the maintenance dose is administered on day 4 and thereafter.

In some embodiments, the invention provides a method of treating pulmonary fibrosis conditions promoted by mechanical injury to the lungs as a result of mechanical ventilation, wherein an NK-1 antagonist (e.g., orvepitant) or a pharmaceutically acceptable salt, solvate or polymorph thereof is administered to a patient in need of such treatment according to a schedule, wherein a least one loading dose is first administered, and, second, at least one therapeutically effect maintenance dose is administered.

In another embodiment, the method further comprises administering a second loading dose prior to administering the maintenance dose. In one embodiment, the loading dose is three times the maintenance dose and the second loading dose is two times the maintenance dose.

In a further embodiment, the therapeutically effective maintenance dose is 10 mg, about 15 mg, about 20 mg, about 25 mg, about 26 mg, about 27 mg, about 28 mg, about 29 mg, about 30 mg, about 31 mg, about 32 mg, about 33 mg, about 34 mg, about 35 mg, about 40 mg, about 45 mg, about 50 mg, about 55 mg, or about 60 mg administered one or more times a day.

In a further embodiment, the therapeutically effective maintenance dose comprises a dosage from 1 to 60 mg, more preferably 2.5 to 60 mg, more preferably 10 to 60 mg, more preferably 10 to 40 mg, more preferably 20 to 40 mg, more preferably 10 to 30 mg, more preferably 25 to 35 mg.

In another embodiment, the therapeutically effective maintenance dose is administered once a day, once every other day, once every third day, once every fourth day, or once a week.

In some embodiments, the therapeutically effective dose of orvepitant is administered once a day, or one or more times a day, or one or more times a week sufficient to achieve and to maintain a plasma concentration of greater than 70 ng/mL.

Thus, the invention further provides a pharmaceutical composition comprising orvepitant, wherein the composition when administered to a human provides a blood plasma concentration of orvepitant of greater than 70 ng/mL between the dosing interval and when the composition is administered to provide an effective daily dose of orvepitant of about 10 mg to 60 mg.

In some embodiments, the therapeutically effective dose of orvepitant is administered once a day, or one or more times a day, or one or more times a week sufficient to achieve a NK-1 receptor occupancy of orvepitant of greater than 99.9%. Thus, the invention further provides a pharmaceutical composition comprising orvepitant, wherein the composition provides when administered to a human, a NK-1 receptor occupancy of orvepitant greater than 99.9% and when the composition is administered to provide an effective daily dose of orvepitant of about 30 mg to 60 mg.

It will be appreciated that it may be necessary to make routine variations to the dosage, depending on the age and condition of the patient and the precise dosage will be ultimately at the discretion of the attendant physician or veterinarian. The dosage will also depend on the route of administration.

If desired, other therapeutic agents can be employed in conjunction with those provided in the above-described compositions. The amount of active ingredients that may be combined with the carrier materials to produce a single dosage form will vary depending upon the host treated, the nature of the disease, disorder, or condition, and the nature of the active ingredients.

The pharmaceutical compositions of the present invention may be given in a single dose or multiple doses daily.

It is understood, however, that a specific dose level for any particular patient will vary depending upon a variety of factors, including the activity of the specific active agent; the age, body weight, general health, sex and diet of the patient; the time of administration; the rate of excretion; possible drug combinations; the severity of the particular condition being treated; and the form of administration. One of ordinary skill in the art would appreciate the variability of such factors and would be able to establish specific dose levels using no more than routine experimentation.

Pharmacokinetic parameters such as bioavailability, absorption rate constant, apparent volume of distribution, unbound fraction, total clearance, fraction excreted unchanged, first-pass metabolism, elimination rate constant, elimination half-life, and mean residence time are well known in the art.

The optimal formulations can be determined by one skilled in the art depending upon considerations such as the particular ingredients and the desired dosage. See, for example, *Remington's Pharmaceutical Sciences*, 18th ed. (1990, Mack Publishing Co., Easton, Pa. 18042), pp. 1435-1712, and "Harry's Cosmeticology", 8th ed. (2000, Chemical Publishing Co., Inc., New York, N.Y. 10016), the disclosure of each of which is hereby incorporated by reference herein in its entirety. Such formulations may influence the physical state, stability, rate of in vivo release, and rate of in vivo clearance.

In particular, the ability to formulate compositions capable of long-term storage, without pre-mixing or compounding requirements prior to application, are also contemplated. Specifically, the present compositions remain unexpectedly stable in storage for periods including between about 3 months and about 3 years, about 3 months and about 2.5 years, between about 3 months and about 2 years, between about 3 months and about 20 months, and alternately any time period between about 6 months and about 18 months.

Thus, in another aspect, the invention provides a pharmaceutical composition comprising an NK-1 receptor antagonist and one or more pharmaceutically acceptable carriers or excipients for use in treating mechanical injury to the lungs in the subset of patients with pulmonary fibrosis conditions who cough, as well as patients receiving mechanical ventilation with either pulmonary fibrosis conditions or with acute respiratory failure.

Combination Therapies with NK-1 Receptor Antagonists and Other Therapeutic Agents It will be appreciated by those skilled in the art that an NK-1 receptor antagonist according to the invention may advantageously be used in combination with one or more other therapeutic agents. For instance with: P2X3 antagonists such as gefapixant (also called AF-219 and MK-7264), sivopixant (also called S-600918), eliapixant (also called BAY1817080), filapixant (also called BAY-1902607), BLU-5937 and AF130; mast cell stabilisers such as disodium cromoglycate (PA101 also called RVT-1601); TRPM8 receptor agonists such as AX8 and AX10; sodium channel blockers such as NTX-1175 (also called NOC-100); GABA analogues for example gabapentin and pregabalin; NDMA receptor antagonists for example dextromethorphan, NP-120 (ifenprodil); opioids such as codeine, hydrocodone and morphine; opioid mu antagonists/opioid kappa agonists such as nalbuphine; corticosteroids, such as dexamethasone, methylprednisolone, prednisolone or hydrocortisone; immunomodulatory drugs (IMiDs) such as thalidomide and IW001; small molecule tyrosine-kinase inhibitors such as nintedanib or deuterated nintedanib; lysophosphatidic acid (LPA)-1 antagonists such as AM095, AM152, AM966, Ki16425, SAR100842, BMS-986020, BMS-986278 and UD-009; LPA-2 receptor agonists such as (R)-1-phenylethyl-5-(4-biphenyl-4-cyclopropanecarboxylic acid)-3-methylisoxazole-4-yl carbamate sodium salt; LPA-2 antagonists such as H2L5186303; NADPH oxidase (NOX)-4 inhibitors such as GLX351322 and 2-(2-chlorophenyl)-4-[3-(dimethylamino)phenyl]-5-methyl-1H-pyrazolo[4,3-C]pyridine-3,6(2H,5H)-dione; NOX-1,4 inhibitors such as GKT831 and setanaxib; and NOX inhibitors such as VAS2870 and GKT137831; c-Jun amino-terminal kinase (JNK) inhibitors such as tanzisertib (CC-930) and CC-90001; compounds of unknown mechanism such as 3-pentylbenzenacetic acid sodium salt, pirfenidone or deuterated pirfenidone, NIP292 and ORIN1001; type-A selective endothelin receptor antagonists such as ambrisentan; copper chelators such as tetrathiomolybdate; anti-IL-4 receptor antibodies (that therefore target IL-4 and IL-13) such as dupilumab; bispeciifc anti-IL-4/IL-13 antibodies such as SAR156597 and lebrikizumab; dual endothelin receptor antagonists such as bosentan, macitentan, tezosentan, macitentan; anti-CC-chemokine ligand 2 (CCL2) antibodies such as carlumab (CNTO 888); chemokine receptor type 4 antibodies such as AD-114; anti-IL-13 antibodies such as QAX576I, lebrikizumab and tralokinumab; anti-L13 antibodies linked to a mutated form of pseudomonas exotoxin A such as cintredekin besudotox; anti-transforming growth factor-beta (TGFβ) antibodies such as fresolimumab (GC1008) and siRNAs such as TRK-250/BNC-1021; anti-connective tissue growth factor monoclonal antibodies such as pamrevlumab (FG-3019); anti-αvβ6 integrin antibodies such as 264RAD, STX-100 and BG00011; integrin αvβ6 antagonists such as GSK 3008348: dual integrin αvβ1/αvβ6 antagonists such as PLN-74809; anti-lysyl oxidase-like 2 (LOXL2) antibodies such as simtuzumab; anti-chemokine (C-C motif) CCL-24 (also known as myeloid progenitor inhibitory factor 2 (MPIF-2) or eosinophil chemotactic protein 2 (eotaxin-2)) antibodies such as CM-101; purified bovine Type V Collagen oral solutions such as IW00; with synthetic analogues of pentraxin-2 (PTX2) modulators of fibrotic tissue such as the recombinant form of the human PTX2 protein (also known as serum amyloid P) such as PRM-151; NK-1 agonists such as [Sar9,Met(O2)11]-Substance P (NAS911B); a tetra-substituted porphyrin derivative containing manganese (III); antagonists of the leukotriene (LT) receptor combined with phosphodiesterases (PDE)-3,4; 5-lipoxygenase (5-LO) inhibitors such as tipelukast (MN-001); peroxisome proliferator-activated receptor pan-agonists such as 1-(6-Benzothiazolylsulfonyl)-5-chloro-1H-indole-2-butanoic acid; angiotensin II type-2 receptor (AT]-2 receptor agonists such as 3-[4-(1H-imidazol-1-ylmethyl)phenyl]-5-(2-methylpropyl)thiophene-2-[(N-butyloxylcarbamate)-sulphonam ide] sodium salt and VP01 (also called C21 or Compound 21); AT-2 receptor antagonists such as PD-123319; AT-1 receptor antagonists such as olmesartan medoxomil; PDE-4B inhibitors such as BI 1,015,550, PDE-5 inhibitors such as sildenafil, tadalafil and vardenafil; BCR-ABL tyrosine kinase inhibitors such as bafetinib (INNO-406), bosutinib (SKI-606), dasatinib (BMS-345825), imatinib, nilotinib (AMN107) and ponatinib (AP24534); synthetic prostacyclin analogues such as iloprost and cisaprost; with synthetic analogues of prostacyclin such as treprostinil; lecithinized superoxide dismutase; beta-2 adrenoceptor agonists such as albuterol (also known as salbutamol); mannose-6-phosphate derivatives such as PXS-25; galectin-3 inhibitors such as GB0139 (also called TD139); combinations of pentoxifylline and vitamin E such as PTL-202; MAPKAP Kinase 2 (MK2) inhibitors such as MMI-0100; hedgehog pathway inhibitors such as vismodegib; cysteine pro-drugs and glutathione precursors such as N-acetylcysteine; leukotriene A4 hydrolase (LTA4H) inhibitors such as acebilustat (CTX-4430); proton pump inhibitors such as omeprazole, lansoprazole, dexlansoprazole, rabeprazole, pantoprazole and esomeprazole; autotaxin inhibitors such as ziritaxestat (also called GLPG1690) and BBT-877; recombinant human soluble thrombomodulin such as ART-123; ROCK-1,2 dual inhibitors such as Fasudil, Ripasudil (K-115), Netarsudil (AR-13324); ROCK-2 inhibitors such as KD-025 (also called SLX-2119); anti-TNF antibodies such as etanercept, infliximab, adalimumab, certolizumab pegol and golimumab; PI3Kinase/mTOR inhibitors such as omipalisib (GSK2126458) and HEC 68498; hemoglobin modifiers such as GBT440; mesenchymal stem cell therapies such as Ref acell-IPF; metalloporphyrins such as AEOL-10150; complement factor C3 inhibitors such as APL-1 and tryptophan hydroxylase 1 (TPH1) inhibitors such as KAR-5585; anti-B cell antibodies such as rituximab; anti-oxidants such as N-acetylcysteine (NAC) and AEOL 10150; and NAC in combination with hemorheologic agents such as pentoxifylline, such as PTL-202; IL-6 inhibitors (targeting either receptor or cytokine) such as tocilizumab, siltuximab, sarilumab, olokizumab, elsilimomab, levilimab; Hsp47 siRNAs such as ND-L02-s0201; mTOR inhibitors such as rapamycin (sirolimus); GPR84 inhibitors such as GLPG1205 and PBI-4050; anti-VEGF antibodies such as bevacizumab; angiogenesis inhibitors such as IBIO-CFB03; calpain inhibitors such as BLD-2660; CD20 antibodies such as rituximab; Src and Bcr-Abl tyrosine-kinase inhibitors such as saracatinib; B-cell activating factor receptor-blocking antibodies such as VAY736; CHIT1/AMCase inhibitors such as GLPG4716; porcupine inhibitors such as RXC006; and BAFF-R antibodies such as lanalumab.

In some embodiments the therapeutic agents which may advantageously be used in combination with the NK-1 antagonists are selected from P2X3 purinergic receptor antagonists such as 5-(2,4-diaminopyrimidin-5-yloxy)-4-isoproply-2-methoxy-benzenesulfonamide (gefapixant), AF-130, sivopixant, eliapixant, filapixant or BLU-5937, as well as nintedanib, pirfenidone, pamrevlumab; the recombinant form of the human PTX2 protein called PRM-151, treprostinil, thalidomide, gabapentin, pregabalin, codeine and ifenprodil.

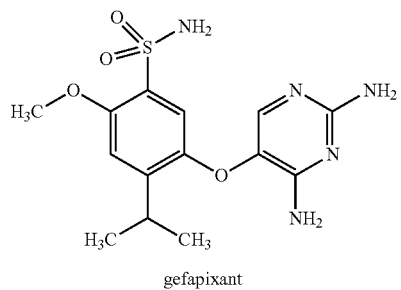

gefapixant

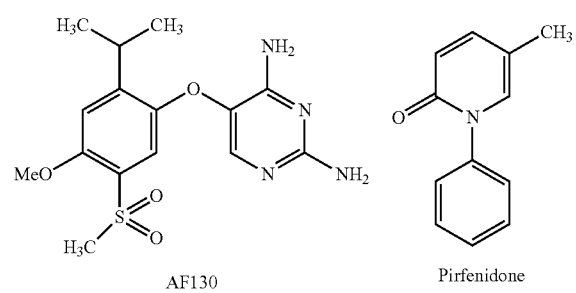

AF130

Pirfenidone

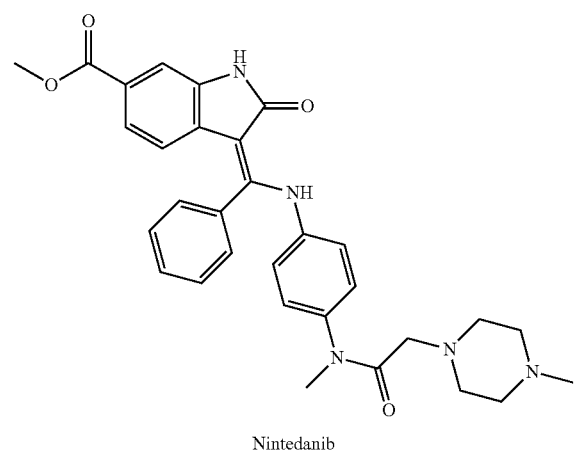

Nintedanib

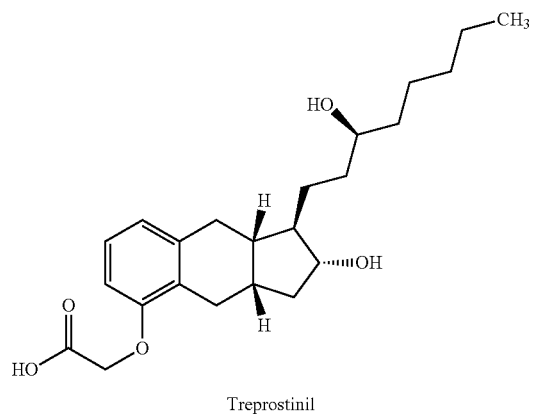

Treprostinil

-continued

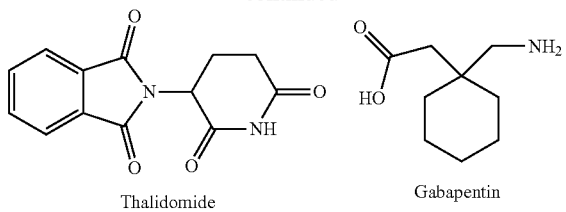

Thalidomide

Gabapentin

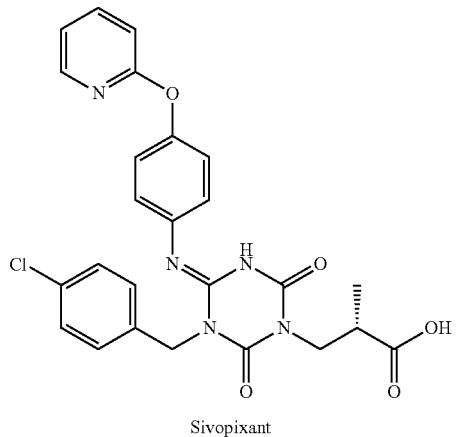

Pregabalin

Codeine

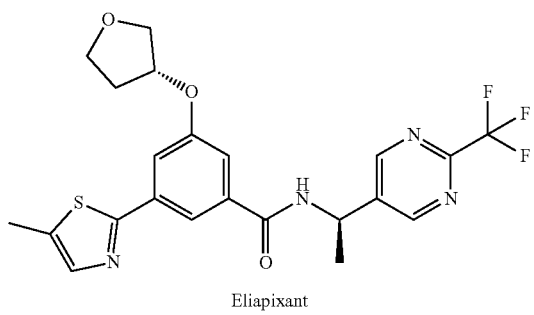

Sivopixant

Eliapixant

-continued

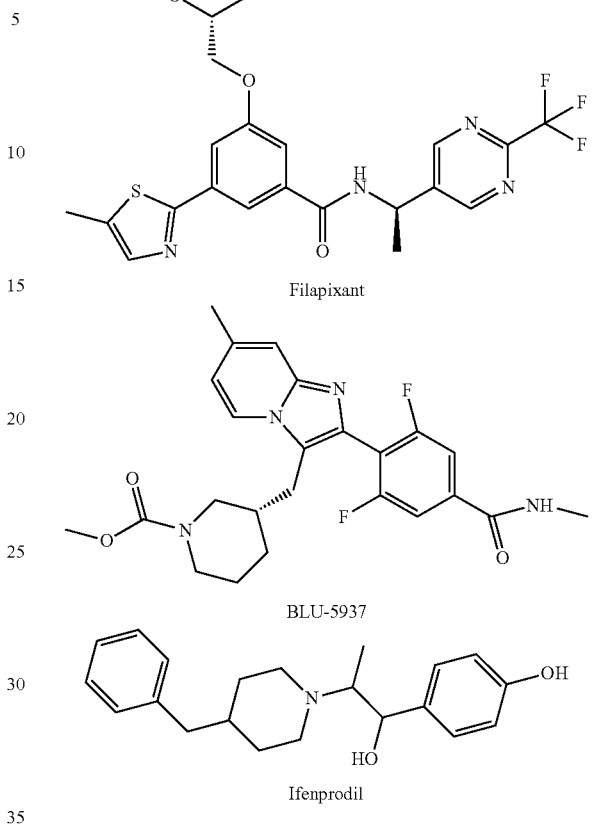

Filapixant

BLU-5937

Ifenprodil

The following examples illustrate the invention without limiting the scope thereof.

Biological Studies

Assays for Pulmonary Fibrosis Promoted by Mechanical Injury to the Lungs.

The use of NK-1 receptor antagonists (e.g., orvepitant) as a treatment for pulmonary fibrosis conditions promoted by mechanical injury to the lungs in the subset of patients with ILDs, IIPs, IPF, NSIP, sarcoidosis, CT-ILD, SSc-ILD, RA-ILD, pleural fibrosis or bronchiolitis obliterans that cough, or patients with ILDs, IIPs, IPF, NSIP, sarcoidosis, CT-ILD, SSc-ILD, RA-ILD, coronavirus infection including COVID-19, SARS or MERS, pleural fibrosis, bronchiolitis obliterans or a patient with acute respiratory failure receiving mechanical ventilation, is assessed by determining the effects of an NK-1 receptor antagonist (e.g., orvepitant) in one or more assays of mechanical injury to the lungs. Assays involve human or animal primary cells or cell-lines, ex vivo explanted human healthy normal or IPF (or other pulmonary fibrosis condition) lung tissue, or/and lung tissue from healthy animals or/and animal lung fibrosis models or/and animal models of injurious mechanical ventilation. Lung tissue from these sources are prepared as lung strips or precision cut lung tissue slices.

The effect of the NK-1 receptor antagonist (e.g., orvepitant) in one or more assays is investigated following activation by SP, that is added to simulate release as a result of mechanical injury to the lungs. A specific NK-1 receptor agonist such as GR73632 is used as an activator in these studies as an alternative to SP.

Types of human primary cells or human cell lines that are used in these investigations include:
- Human epithelial cell lines such as BEAS-2B, H358, HPL1D, VA10, 16HBE14o and A549, or human primary lung normal epithelial cells or human primary lung epithelial cells donated by patients with a pulmonary fibrosis condition
- Human monocyte/macrophage cell lines such as THP-1 and U937 cells, human primary normal lung macrophage cells or human primary lung macrophage cells donated by patients with a pulmonary fibrosis condition, human primary normal monocyte cells or human primary monocyte cells donated by patients with a pulmonary fibrosis condition
- Human mast cell lines such as HMC-1, LAD2, and LUVA cells, human primary lung normal mast cells or human primary lung mast cells from pulmonary fibrosis donors
- Human T-cell lines such as human primary lung isolated T cells or human primary lung isolated T-cells donated by patients with a pulmonary fibrosis condition
- Human lung fibroblast cell lines such as W138, MRC5, HFL1, HDF and IMR90, or human primary lung normal fibroblasts or human primary lung fibroblasts donated by patients with a pulmonary fibrosis condition
- Human lung endothelial cells lines such as PCS-100-022, or human primary lung normal endothelial cells or human primary lung endothelial cells donated by patients with a pulmonary fibrosis condition
- Co-culture of two or more different combinations of human lung cells for example from: epithelial cells, fibroblasts, myofibroblasts, macrophages, mast cells, T-cells and endothelial cells The enhanced amount of cytokines, chemokines, growth factors, mucins, extracellular matrix (ECM) proteins, SP, and other mediators produced by the cells/tissues following mechanical injury or as a result of replicating SP release from neuronal and extra-neuronal sources (as a result of mechanical injury), and the proinflammatory and profibrotic effects these molecules promote, is demonstrated, as well as the inhibition of the release of these mediators and their effects by administration of an NK-1 receptor antagonist (e.g., orvepitant).

Cytokines to be assayed may include IL-1α/·, IL-6, and IL-17A that are proinflammatory mediators released by various cells including neutrophils, monocytes, macrophages and T cells that can contribute to innate and adaptive immune responses by activating immune cells and other cell types to induce both further proinflammatory mediators as well as profibrotic mediators that may include growth factors such as TGFβ. The cytokines can also have a direct stimulatory effect on fibroblasts which respond by proliferating differentiating to myofibroblasts, and expressing profibrotic mediators such as the growth factor TGF and extracellular matrix proteins (ECMs), leading to extracellular matrix deposition and the development and progression of fibrosis.

Chemokines to be assayed include MCP-1 (CCL-2), CXCL1 and MIP-2, these are proinflammatory mediators that are released by monocytes, macrophages and other cell types and contribute to innate and adaptive immune responses by recruiting innate immune cells and memory T cells which contribute to progressive fibrosis by releasing proteins that induce production of further proinflammatory mediators as well as profibrotic mediators such as growth factors in multiple cell types including by fibroblasts and myofibroblasts. Growth factors to be assayed including TGF are important profibrotic mediators released by multiple cell types including fibroblasts, myofibroblasts, epithelial cells, macrophages and T cells and contribute significantly to proinflammatory and profibrotic responses by regulating the proliferation, differentiation and survival of multiple cell types. TGF is a master regulator of multiple signalling pathways in mesenchymal cells such as fibroblasts and regulates the growth and expansion of myofibroblasts including the synthesis of extracellular matrix proteins and significantly contributing to the growth and progression of fibrotic lesions. Levels of phosphoSMAD2 (pSMAD2) as a marker of TGF pathway activation is assayed.

The polymeric secreted mucin Muc5b to be assayed is important in determining the elastic properties of airway mucus which is an important component of the mucociliary clearance mechanism and thereby contributes to airway defence in the lung. Muc5b may also have direct or indirect effects on immune cell functions in the lung including via effects on macrophage activation, phagocytosis and cytokine production including reduced IL-23 release. Such atypical macrophage responses and functions can enhance proinflammatory responses in other cells including the release of mediators with profibrotic effects on fibroblasts contributing to fibrosis development and progression.

The ECM proteins to be assayed include collagen type 1a1 and collagen type 3a1 that are deposited into insoluble collagen fibres in the ECM and form a significant volume of a growing fibrotic lesion. The collagen-rich fibrotic scarring in the lung develops in the interstitium replacing and displacing alveoli thus progressively impairing gas exchange and contributing significantly to the pathogenesis of fibrotic lung conditions.

Other proinflammatory and profibrotic factors to be assayed are soluble RAGE, and soluble ICAM. Membrane-bound ICAM will be determined as a marker of cellular activation on cells such as alveolar macrophages, and Type 1 and 2 alveolar epithelial cells.

Myeloperoxidase (MPO) activity is determined as a measure of pulmonary inflammation.

WBC cell populations to be counted will include neutrophils, inflammatory monocytes (for example lung Ly6C high inflammatory [Ly6C$^{hi}$] monocytes) and alveolar macrophages.

In the case of animal models of mechanical lung injury the levels of these mediators and WBCs will be determined in bronchoalveolar lavage fluid (BAL), lung tissue and plasma/serum.

The appropriate assay technology is used for these studies, for instance mRNA profiling, enzyme-linked immunosorbent assay (ELISA), Meso Scale Discovery (MSD) assays, flow-cytometry and immunohistochemistry (IHC).

In Vivo Models of Mechanical Injury to the Lungs

Bleomycin-induced lung injury in rodents is a recognised model to evaluate therapeutic agents for pulmonary fibrosis conditions. Pulmonary fibrosis in this model is established by intratracheal administration of clinical grade bleomycin. The effects of coughing on the progression of the pulmonary fibrosis is then investigated by comparing a group of animals inhaling vehicle to group(s) inhaling pro-tussive substances such as citric acid, capsaicin or allylisothiocyanate. The effects of therapy with an NK-1 antagonist (e.g., orvepitant) on development of the pulmonary fibrosis in the model is examined using assays for the mediators and cell-types described above. Lung hydroxyproline is also be determined in this model.

In another study animals are subjected to mechanical ventilation to induce mechanical injury to the lungs, and the levels of proinflammatory and profibrotic cytokines, chemokines, growth factors, mucins, ECM proteins, other proinflammatory and profibrotic factors, MPO activity, WBC populations and SP are determined in bronchoalveolar lavage fluid (BAL), plasma/serum and lung tissue. In such models physiological measurements to assess lung injury such as peak inspiratory pressure, blood pressure, respiratory mechanics (elastance and resistance) and blood gases are determined. The effects of the NK-1 receptor antagonist (e.g. orvepitant) in reducing the expression of these mediators and enzyme activity, and effects on the physiological measurements are assessed by prophylactic administration prior to the mechanical ventilation.

Lung tissue strips isolated from either of these models may be used in the ex-vivo assays described above.

EXAMPLES

Preclinical Studies

NK-1 antagonists as a method of treating pulmonary fibrosis conditions by reducing mechanical injury to the lungs induced by mechanical ventilation.

Orvepitant was evaluated in a VILI mouse model of mechanical injury to the lungs.

Study Design

Male C57/BL6 mice were pre-treated with oral orvepitant (250 mg/kg) or vehicle control (10 ml/kg, 0.1% tween 80:0.5% hydroxypropyl methylcellulose [HPMC]), approximately 30 minutes before initiation of experimental ventilation.

Mice were anesthetized and tracheotomised for ventilation. The left carotid artery was cannulated to monitor blood pressure (BP), infuse heparinised saline (0.4 ml/hr of 10 units/ml of heparin), and measure sequential blood gas analyses. Airway pressure was monitored continuously, while respiratory mechanics including respiratory resistance (Rrs) and elastance (Ers), were measured at predetermined intervals by end-inflation occlusion. Vehicle-treated or orvepitant-treated animals were ventilated with high tidal volume (33-37 ml/kg) for up to 150 minutes or until a mortality surrogate (increase of >25% peak inspiratory pressure) was reached. As a control group, vehicle-treated animals only were ventilated with low tidal volume (8-9 ml/kg) to confirm the impact of injurious ventilation. Following termination, bronchoalveolar lavage fluid (BAL) was collected for analysis and lungs were processed for flow cytometric evaluation of leukocyte numbers and expression of ICAM-1 on alveolar macrophages and epithelial cells.

Data were evaluated for normality by Shapiro-Wilk test of residuals and QQ plots. Normally distributed data were evaluated by t-test for end-point analysis, or 2-way ANOVA for time courses. Non-normally distributed data were evaluated by Mann-Whitney U test. N=6-7 animals for each dataset.

Results

Physiological variables. Peak inspiratory pressure was identical between vehicle and orvepitant pre-treated animals at the start of ventilation. Pressure decreased initially in both groups and remained stable until ~90 minutes when it started to increase, indicating the development of lung injury. Peak inspiratory pressure increased more markedly in vehicle-treated animals than those treated with orvepitant, such that the majority of vehicle treated animals developed substantial injury at or before 150 minutes, and the course of pressure change over time was significantly different between groups (FIG. 1). The 'end' peak inspiratory pressure, which represents the final value recorded (either 150 minutes or when the mortality surrogate was reached if this occurred earlier) was also significantly higher in vehicle-treated animals than those receiving orvepitant (FIG. 1). Changes in respiratory system elastance over time mirrored the peak inspiratory pressure, although differences between groups did not quite achieve statistical significance (FIG. 1). As expected, low tidal volume ventilation did not induce substantial changes in physiological variables over time (data not shown).

Flow cytometric analyses. Lung cell suspensions were evaluated for quantification of neutrophils and Ly6C high inflammatory (Ly6CN) monocytes by flow cytometry. Treatment with orvepitant led to a significant decrease in these leukocyte numbers within lung tissue compared to the vehicle control animals (FIG. 2). Activation of alveolar macrophages and type 1 and type 2 epithelial cells was determined by assaying for surface expression of ICAM-1. High tidal volume ventilation induced a substantial upregulation of ICAM-1 expression on all 3 cell types, and this upregulation was significantly attenuated by pre-treatment with orvepitant (FIG. 2).

Bronchoalveolar lavage fluid (BAL) markers. BAL total protein concentration was measured as a marker of alveolar-epithelial barrier permeability. High tidal volume ventilation in vehicle-treated animals provoked a substantial increase in BAL total protein compared to low tidal volume (indicated by dotted line on the Figures); the increase in BAL total protein concentration was significantly attenuated by orvepitant pre-treatment (FIG. 3). Similarly, the proinflammatory mediators (MCP-1 [CCL-2], IL-6) and profibrotic factor (TGF-β) were upregulated following high tidal volume ventilation and the increases were all significantly attenuated by orvepitant treatment (FIG. 3).

CONCLUSION

Pretreatment of mice with oral orvepitant led to substantial, significant attenuation of mechanical lung injury induced by mechanical ventilation. The expected increase in proinflammatory and profibrotic mediators linked to the pathogenesis of pulmonary fibrosis conditions, namely: neutrophils (Obavashi, 1997), Ly6C high inflammatory monocytes (Zhang, 2018), ICAM-1 (Paine & Ward, 1999), MCP-1 (h onaga, 1994), IL-6 (Kolahian, 2016), and TGF-β (Fernandez & EickebeR, 2012), were all significantly attenuated with orvepitant administration in this model of mechanically induced pulmonary injury where the lungs have been expanded beyond their limit of physical tolerance. Such injury would also occur in patients with pulmonary fibrosis conditions that cough, as their stiffened and scarred lungs would be particularly susceptible to the mechanical tissue damage that coughing induces.

In summary given this model recapitulates the proinflammatory and profibrotic cascades linked to the development of pulmonary fibrosis conditions, then the data generated unequivocally demonstrates that NK-1 antagonists have potential to be administered as a method of treatment of pulmonary fibrosis conditions promoted by mechanical injury to the lungs.

Clinical Studies

NK-1 Receptor Antagonists as a Method of Treating Pulmonary Fibrosis Due to Mechanical Injury to the Lungs in the Subset of Patients with the Pulmonary Fibrosis Condition IPF Who Cough The efficacy of an NK-1 receptor antagonist (e.g. orvepitant) as a monotherapy or as an add-on to a standard-of-care IPF treatment, such as pirfenidone and/or nintedanib that patients have been taking at a stable dose, as a treatment for pulmonary fibrosis progression promoted by mechanical injury to the lungs in the subset of patients with the pulmonary fibrosis condition IPF who cough, is evaluated in a placebo controlled, double-blind, randomised study ranging in duration from 4 to 52 weeks, in patients who have an established diagnosis of IPF. Cough burden that reflects the level of mechanical injury to the lungs in these patients is assessed at baseline and randomisation is stratified such that this measure is balanced across the arms of the study.

Efficacy is evaluated as the change from baseline to the study using appropriate outcome measures, such as decline in percent predicted forced vital capacity (FVC) or/and other appropriate assessment, as well as measures that assess cough burden, biomarkers and imaging technologies.

Prespecified sub-group analysis is used to evaluate the study outcomes according to the measure of cough burden at baseline.

NK-1 Antagonists as a Method of Treating the Pulmonary Fibrosis Condition Due to Mechanical Injury to the Lungs in Patients Receiving Mechanical Ventilation The efficacy of an NK-1 receptor antagonist (e.g. orvepitant) as a method for treating the pulmonary fibrosis condition due to mechanical injury to the lungs in mechanically ventilated patients is evaluated in a randomised, double-blind placebo-controlled study in which administration of an NK-1 receptor antagonist (e.g. orvepitant) or placebo is added to standard of care. Patients requiring airway mechanical ventilation are randomised to orvepitant or placebo for 1-4 weeks. Efficacy is established if there is a significant difference in favour of the NK-1 receptor antagonist (e.g. orvepitant) in one or more study outcomes that may include progression to ventilator induced lung injury, duration of intensive care unit admission and duration of mechanical ventilation, development of a pulmonary fibrosis condition or death. Other appropriate assessments including biomarkers and imaging technologies may be used as assessments.

Pharmaceutical Compositions

For the treatment of medical conditions according to the present invention the NK1 receptor antagonist will normally, but not necessarily, be formulated into pharmaceutical compositions prior to administration to a patient.

Thus, for example orvepitant maleate Form 1 have been formulated as white to off-white, film-coated round tablets containing 10 mg, 20 mg and 30 mg of orvepitant which provide an immediate release of the active ingredient for oral administration.

The tablet core is manufactured from a granule containing 30.00% w/w of the orvepitant maleate Form 1 drug substance and detailed in Table 1.

TABLE 1

Composition for Orvepitant maleate Form 1, 30.00% w/w Granulation Formulation

| Component | Master Unit Formula Quantity (% w/w) | Equivalent Weight (mg) per Tablet | | | Function |
|---|---|---|---|---|---|
| | | 10 mg | 20 mg | 30 mg | |
| Orvepitant maleate maleate Form 1, Drug Substance | 30.00[1] | 11.85[2] | 23.70[3] | 35.54[4] | Active Substance |
| Hypromellose 2910 | 5.00 | 1.97 | 3.94 | 5.92 | Binder |

TABLE 1-continued

Composition for Orvepitant maleate Form 1, 30.00% w/w Granulation Formulation

| Component | Master Unit Formula Quantity (% w/w) | Equivalent Weight (mg) per Tablet | | | Function |
|---|---|---|---|---|---|
| | | 10 mg | 20 mg | 30 mg | |
| Lactose monohydrate | 33.50 | 13.23 | 26.46 | 39.7 | Diluent |
| Microcrystalline cellulose | 30.00 | 11.85 | 23.7 | 35.54 | Diluent |
| Croscarmellose Sodium | 1.50 | 0.59 | 1.18 | 1.78 | Disintegrant |

[1]Corresponding to 25.32% w/w as orvepitant
[2]Corresponding to 10 mg as orvepitant
[3]Corresponding to 20 mg as orvepitant
[4]Corresponding to 30 mg as orvepitant The complete statement of the components and quantitative composition of orvepitant maleate Form 1 tablets, 10 mg, 20 mg and 30 mg is given below in Table 2.

TABLE 2

Composition Table for Orvepitant Tablets, 10 mg, 20 mg and 30 mg

| Component | Quantity | | | Functionality |
|---|---|---|---|---|
| | 10 mg | 20 mg | 30 mg | |
| Orvepitant maleate Form 1[1] granule (30.00% w/w) | 39.49 | 78.98 | 118.48 | Active |
| Lactose monohydrate | 188.51 | 149.02 | 109.52 | Filler |
| Microcrystalline cellulose | 60.00 | 60.00 | 60.00 | Filler |
| Croscarmellose Sodium | 9.00 | 9.00 | 9.00 | Disintegrant |
| Magnesium stearate | 3.00 | 3.00 | 3.00 | Lubricant |
| Purified water (removed during processing) | qs | qs | qs | Granulating fluid |
| Total Unit Dose | 300.0 | 300.0 | 300.0 | — |
| Opadry ® White | 9.0[2] | 9.0[2] | 9.0[2] | Coating agent |
| Purified water | qs | qs | qs | Suspending agent |

[1]The actual quantity of orvepitant maleate Form 1 may be adjusted based on the purity of the input drug substance.
[2]The weight of film coat applied per tablet may vary depending on the efficiency of the process but is typically 3% w/w of tablet core weight.

Orvepitant maleate Form 1 tablets, 10 mg, 20 mg and 30 mg were manufactured using wet granulation, dry blending, tablet compression and film coating processes.

Drug substance, lactose monohydrate, microcrystalline cellulose and croscarmellose sodium were sieved and dry mixed into the high shear mixer granulator. The granulation water was sprayed onto the drug substance, lactose monohydrate, microcrystalline cellulose and croscarmellose sodium dry blend. The wet granule was dried in a fluid bed dryer, milled using a conical mill and blended into a bin blender with lactose monohydrate, microcrystalline cellulose and croscarmellose sodium. Magnesium stearate was added for lubrication into the bin blender and the mixture was blended.

The blend was compressed using a suitable rotary tablet compression machine to obtain uncoated tablets. The tablets were film coated in a suitable pan coater.

The invention claimed is:

1. A method of treating pulmonary fibrosis promoted by mechanical injury to the lungs of a patient with idiopathic pulmonary fibrosis (IPF), said method comprising administering to said patient a therapeutically effective amount of orvepitant or a pharmaceutically acceptable salt thereof.

2. The method of claim 1, wherein the mechanical injury to the lungs is promoted by mechanical ventilation of a patient with acute respiratory failure.

3. The method of claim 1, wherein the mechanical injury to the lungs is promoted by mechanical ventilation of a patient with idiopathic pulmonary fibrosis (IPF).

4. The method of claim 1, wherein the pharmaceutical acceptable salt is or comprises orvepitant maleate.

5. The method of claim 4, wherein the orvepitant maleate is in as anhydrous crystalline form.

6. The method of claim 4, wherein the orvepitant maleate is in as anhydrous crystalline Form 1.

7. The method of claim 1, wherein the mechanical injury to the lungs is induced by coughing in patients diagnosed with idiopathic pulmonary fibrosis (IPF).

8. The method of claim 7, wherein the pharmaceutically acceptable salt is or comprises orvepitant maleate.

9. The method of claim 8, wherein orvepitant maleate is in as anhydrous crystalline form.

10. The method of claim 8, wherein orvepitant maleate is in anhydrous crystalline Form 1.

11. The method of claim 1, comprising administering to a human in need thereof a therapeutically effective amount of orvepitant or a pharmaceutically acceptable salt thereof in combination with one or more therapeutic agents selected from pirfenidone, nintedanib, BMS-986278, saracatinib, CC9000, BI1015550, treprostinil, thalidomide, gabapentin, pregabalin, codeine, gefapixant, BLU-5937, nalbuphine and ifenprodil.

* * * * *